(12) United States Patent
Roukes et al.

(10) Patent No.: US 9,347,815 B2
(45) Date of Patent: May 24, 2016

(54) SINGLE-PROTEIN NANOMECHANICAL MASS SPECTROMETRY IN REAL TIME

(71) Applicant: California Institute of Technology, Pasadena, CA (US)

(72) Inventors: Michael L. Roukes, Pasadena, CA (US); Mehmet Selim Hanay, Pasadena, CA (US); Scott Kelber, Pasadena, CA (US); Akshay Naik, Bangalore (IN)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 592 days.

(21) Appl. No.: 13/890,087

(22) Filed: May 8, 2013

(65) Prior Publication Data

US 2014/0156224 A1    Jun. 5, 2014

Related U.S. Application Data

(60) Provisional application No. 61/644,916, filed on May 9, 2012.

(51) Int. Cl.
| | |
|---|---|
| G06F 19/00 | (2011.01) |
| G01G 9/00 | (2006.01) |
| H01J 49/34 | (2006.01) |
| G01G 3/16 | (2006.01) |
| G01N 5/02 | (2006.01) |

(52) U.S. Cl.
CPC .. *G01G 9/00* (2013.01); *G01G 3/16* (2013.01); *G01N 5/02* (2013.01); *H01J 49/34* (2013.01)

(58) Field of Classification Search
CPC .......................... H01J 49/0454; H01J 49/0463

USPC ........................................................ 702/18
See application file for complete search history.

(56) References Cited

U.S. PATENT DOCUMENTS

| | | | |
|---|---|---|---|
| 6,722,200 B2 | 4/2004 | Roukes et al. | |
| 7,302,856 B2 | 12/2007 | Tang et al. | |
| 7,330,795 B2 | 2/2008 | Roukes et al. | |
| 7,552,645 B2 | 6/2009 | Bargatin et al. | |
| 7,555,938 B2 | 7/2009 | Bargatin et al. | |
| 7,617,736 B2 | 11/2009 | Tang et al. | |
| 7,724,103 B2 | 5/2010 | Feng et al. | |
| 7,989,198 B2 | 8/2011 | Roukes et al. | |
| 8,044,556 B2 | 10/2011 | Masmanidis et al. | |

(Continued)

FOREIGN PATENT DOCUMENTS

WO    WO 2005/031300 A2    4/2005

OTHER PUBLICATIONS

Allan, D. W. "Statistics of atomic frequency standards". *Proceedings of the IEEE* 54, 221230 (1966).

(Continued)

*Primary Examiner* — Edward Raymond
(74) *Attorney, Agent, or Firm* — The Marbury Law Group, PLLC

(57) ABSTRACT

Methods and devices relating to measuring a landing position and mass of an analyte adsorbed to a nanomechanical resonator by resolving adsorbate-induced frequency shifts in at least two modes of a resonator resonance frequency, where during the resolving of the frequency shifts in the at least two modes analysis is so that the transformation (G) from the fractional-frequency shift pair to the analyte mass-position pair is one-to-one. Complex protein mixtures can be analyzed at high sensitivity and resolution.

40 Claims, 19 Drawing Sheets

(56) References Cited

U.S. PATENT DOCUMENTS

| | | | |
|---|---|---|---|
| 8,227,747 | B2 | 7/2012 | Roukes et al. |
| 8,329,452 | B2 | 12/2012 | Roukes et al. |
| 8,350,578 | B2 | 1/2013 | Sadek et al. |
| 2009/0261241 | A1 | 10/2009 | Roukes et al. |
| 2010/0271003 | A1* | 10/2010 | Jensen et al. ............... 324/76.49 |
| 2012/0272742 | A1 | 11/2012 | Andreucci et al. |

OTHER PUBLICATIONS

Andersson, C.-O, "Mass Spectrometric Studies on Amino Acid and Peptide Derivatives". *Acta Chem Scand.* 12, 1353 (1958).

Azuma, Y. et al., "Recombinant Human Hexamer-Dominant IgM Monoclonal Antibody to Ganglioside GM3 for Treatment of Melanoma", *Clinical Cancer Research 13*, 2745-2750, (2007).

Bacher, G. et al. "Charge-reduced nano electrospray ionization combined with differential mobility analysis of peptides, proteins, glycoproteins, noncovalent protein complexes and viruses". *Journal of Mass Spectrometry* 36, 1038-1052, (2001).

Bargatin, I., et al., "Efficient electrothermal actuation of multiple modes of high-frequency nanoelectromechanical resonators", *Applied Physics Letters 90*, 093116-093113, (2007).

Benesch, J. L. P et al., "Mass spectrometry of macromolecular assemblies: preservation and dissociation". *Current Opinion in Structural Biology* 16,245-251 (2006).

Beynon, J. H. "The use of the mass spectrometer for the identification of organic Compounds", *Microchim. Acta* 44, 437 (1955).

Chiang, C. L., et al. "Control of nucleation and growth of gold nanoparticles in AOT/Span80/isooctane mixed reverse micelles", *J Solid State Chem* 177,3891-3895, (2004).

Chiu, H.-Yet al, "Atomic-Scale Mass Sensing Using Carbon Nanotube Resonators", *Nano Letters* 8,4342-4346, (2008).

Cole, R.B., "Electrospray and Maldi Mass Spectrometry", (Wiley, 2010).

Collins, C., et al., "Differential activation of human and guinea pig complement by pentameric and hexameric IgM", *European Journal of Immunology 32*, 1802-1810, (2002).

Davis, A. C. et al, "IgM—molecular requirements for its assembly and Function", Immunology Today vol. 10,No. 4, pp. 118-128, (1989).

Dohn, Set al., "Mass and position determination of attached particles on cantilever based mass sensors", *Review of Scientific Instruments* 78, 103303 (2007).

Domon, B. et al. "Mass spectrometry and protein analysis", *Science* vol. 312, pp. 212-217 (2006).

Duijn, et al, "Complexes Monitored by Ion Mobility Mass Spectrometry", *Journal of the American Chemical Society* 131, pp. 1452-1459, (2009).

Ekinci, K. L. et al., "Ultrasensitive nanoelectromechanical mass detection", *Applied Physics Letters 84*, pp. 4469-4471 (2004).

Ekinci, K. L. et al., "Ultimate limits to inertial mass sensing based upon nanoelectromechanical systems", *Journal of Applied Physics 95*, pp. 2682-2689 (2004).

Gil-Santos, E. et al. "Nanomechanical mass sensing and stiffness spectrometry based on two-dimensional vibrations of resonant nanowires" *Nat Nano* 5, 641-645 (2010).

Heck, A. J. R. "Native mass spectrometry: a bridge between interactomics and structural Biology", *Nat Methods* 5, pp. 927-933, (2008).

Hughey, C. T., et al., "Production of IgM Hexamers by Normal and Autoimmune B Cells: Implications for the Physiologic Role of Hexameric IgM", *The Journal of Immunology 161*, 4091-4097 (1998).

Ilic, B. et al., "Attogram detection using nanoelectromechanical oscillators", *Journal of Applied Physics* 95, 3694-3703 (2004).

Jensen, K., et al., "An Atomic-resolution nanomechanical mass sensor", *Nature Nanotechnology 3*, 533-537, (2008).

Kharrat, C. et al., "H∞ Loop shaping control for PLL-based mechanical resonance tracking in NEMS resonant mass sensors", *Sensors, 2008 IEEE* 1135:38.

Kim, B., et al. "Cluster size analysis of two-dimensional order in colloidal gold nanoparticle arrays", *Langmuir* 20, 9360-9365, (2004).

Lassagne, B., et al, "Ultrasensitive Mass Sensing with a Nanotube Electromechanical Resonator", *Nano Letters* 8, 3735-3738, (2008).

Li, M. et al, "Ultra-sensitive NEMS-based cantilevers for sensing, scanned probe and very high-frequency applications", *Nat Nano* 2, 114-120 (2007).

Lindhagen-Persson, M., et al., "Amyloid-β Oligomer Specificity Mediated by the IgM Isotype—Implications for a Specific Protective Mechanism Exerted by Endogenous Auto-Antibodies", *PLoS ONE 5*, e13928, (2010).

Loo, J. A. et al., "Electrospray Ionization Mass Spectrometry and Ion Mobility Analysis of the 20S Proteasome Complex", *Journal of the American Society for Mass Spectrometry 16*, 998-1008, (2005).

Mile, E. et al.,"In-plane nanoelectromechanical resonators based on silicon nanowire piezoresistive detection", *Nanotechnology* 21, 165504 (2010).

Naik, A. K., et al., "Towards single-molecule nanomechanical mass spectroscopy", *Nature Nanotechnology 4*, 445-450 (2009).

Oeljeklaus, S. et al., "New dimensions in the study of protein complexes using quantitative mass spectrometry", *Febs Lett 583*, 1674-1683.

Benesch et al. "Protein complexes in the gas phase: Technology for structural genomics and proteomics", *Chem Rev 107*,pp. 3544-3567, (2007).

Schmid, S. et al. "A. Real-time particle mass spectrometry based on resonant micro strings", *Sensors (Basel)* 10, 8092-8100 (2010).

Tanaka, K, "The Origin of Macromolecule Ionization by Laser Irradiation" (Nobel Lecture). *Angewandte Chemie International Edition* 42,3860-3870, (2003).

Westcott, S. L., et al. "Formation and adsorption of clusters of gold nanoparticles onto functionalized silica nanoparticle surfaces", *Langmuir* 14, pp. 5396-5401 (1998).

Yang,Y. T., et al. "Zeptogram-Scale Nanomechanical Mass Sensing", *Nano Letters* 6, 583-586, (2006).

Invitation to pay additional Fees with annexed search report received in connection with international application No. PCT/US2011/040196; mailed Jun. 25, 2014.

* cited by examiner

SINGLE-PROTEIN NANOMECHANICAL MASS SPECTROMETRY IN REAL TIME

CROSS-REFERENCE TO RELATED APPLICATIONS

This application claims priority under 35 U.S.C. §119(e) to U.S. Provisional Application No. 61/644,916, filed May 9, 2012, which is incorporated herein by reference in its entirety for all purposes.

STATEMENT REGARDING FEDERALLY SPONSORED RESEARCH OR DEVELOPMENT

This invention was made with government support under grant number R01-GM085666-01A1Z from the National Institutes of Health and grant number DBI-0821863 from the National Science Foundation. The government has certain rights in the invention.

BACKGROUND

Nanoelectromechanical system (NEMS) resonators enable mass detection with exceptional sensitivity. This has recently culminated in mass resolution at the single-molecule level, where simple spectra have been assembled by statistical analysis from only a few hundred molecular adsorption events.

Mass spectrometry (MS)—the identification of species through molecular mass measurements—is an important analytical tool in chemical and biological research. Since its first applications to organic compounds more than a half century ago, it has assumed an increasingly dominant role in the life sciences and medicine and is now arguably a mainstay of proteomics. Critical to such measurements are spectrometers that are capable of high resolution in the very large mass range, such as above several hundred kDa, which is at or beyond the limit of many conventional MS techniques. NEMS-MS has been described previously for example in U.S. Application Publication No. 2012/0272742 and U.S. Pat. Nos. 7,302,856; 8,227,747; 7,989,198; 7,617,736; 7,552,645; 8,044,556; 8,350,578; 7,724,103; 7,555,938; 7,330,795; 6,722,200 and 8,329,452.

NEMS resonators can be used for mass detection of an analyte. Upon adsorption onto a NEMS resonator, analytes can precipitously downshift a resonant frequency of the resonator. Despite the impressive recent improvements in mass resolution and the detection of discrete adsorption events, all measurements to date neither measure the mass of individual analytes, nor can do so in real-time. The reason for this is that the resonant frequency shift induced by analyte adsorption depends upon both the mass of the analyte and its precise location of adsorption upon the NEMS resonator. Until now, it was not possible to measure both mass and position of an adsorbed analyte to a NEMS resonator.

NEMS-MS spectra, albeit not in real time, have previously been achieved by employing the known position-dependent mass responsivity for a doubly-clamped NEMS resonator. See U.S. Pat. No. 8,227,747. In this previous work analytes were delivered such that they accreted uniformly across the device; this foreknowledge allowed the deduction of the constituents of simple mixtures after collection of only several hundred single-molecule adsorption events. (For comparison, conventional mass spectrometry measurements typically involve measurement of ~$10^8$ molecules.) The analysis involved fitting to the statistical ensemble of measured frequency shifts by a rather complex multidimensional minimization procedure to extract the weights of each constituent, that is, to deduce the mass spectrum. These first results provided a conceptual demonstration of the potential of NEMS-MS, but the complexity of this process precluded its application to arbitrarily complex mixtures.

SUMMARY

Embodiments described herein include articles and devices, as well as methods of making and using devices.

One embodiment of the present invention relates to a method comprising measuring a landing position and mass of an analyte adsorbed to a nanomechanical resonator by resolving adsorbate-induced frequency shifts in at least two modes of a resonator resonance frequency, where during the resolving of the frequency shifts in the at least two modes analysis is so that the transformation (G) from the fractional-frequency shift pair to the analyte mass-position pair is one-to-one.

In one embodiment, the measuring comprises transducing the resonator into motion at at least a first frequency mode and a second frequency mode and detecting the frequency shifts in the at least the first frequency mode and the second frequency mode upon adsorption of the analyte.

In one embodiment, the at least the first frequency mode and the second frequency mode are measured simultaneously.

In one embodiment, resonator transduction is controlled and monitored using multimode readout circuitry.

In one embodiment, for each mode a first function generator induces a first signal by exciting a drive electrode at half the resonance frequency and a second function generator induces a second signal by biasing a readout electrode at a frequency slightly detuned from the frequency of the first signal, and the first and second signals generate a mix-down signal of mechanical origin at the readout electrode when the drive frequency matches exactly half of the resonance frequency.

In one embodiment, a low-frequency readout signal is amplified and fed into a lock-in amplifier with a matching external reference generated from the two function generators.

In one embodiment, for the at least the first frequency mode and the second frequency mode, a drive signal and a bias signal are split onto a first path and a second path, and: on the first path, the bias signal and the drive signal are mixed and an output signal is used as a reference for a lock-in amplifier; and on the second path, the drive signals for the at least the first frequency mode and the second frequency mode are combined together with a DC source and the total signal ($V_1(\omega_{d1})+V_2(\omega_{d2})+V_{DC}$) is sent to a gate electrode that capacitively actuates the resonator. The bias signals for the at least the first frequency mode and the second frequency mode are split in a 180° splitter and signals with the same polarity of both modes are combined into a bias 1 signal and a bias 2 signal and sent to the resonator; and at the resonator, a bias 1 electrode is charged to $V_1^+(\omega_{b1})+V_2^+(\omega_{b2})$ and a bias 2 electrode is charged to $V_1^-(\omega_{b1})+V_2^-(\omega_{b2})$.

In one embodiment, a control loop is implemented by reading a signal from the lock-in amplifier on a computer that performs a corrector calculation and sends the signals to the function generators. The lock-in amplifiers and the function generators are connected to the computer by a GPIB interface, and the computer controls the instruments without being connected to the RF signals that are sent to the device.

In one embodiment, the induced frequency shift in the at least the first frequency mode and the second frequency mode is modeled as a random variable with a mean value commensurate with the measured shift and with a dispersion identical with that of the frequency noise.

In one embodiment, frequency noise statistics for the first frequency mode and the second frequency mode are combined into a joint probability density function (JPDF) represented by the formula $$JPDF_{\delta f_1, \delta f_2}(\delta f_1, \delta f_2) = \frac{1}{2\pi\sigma_1\sigma_2\sqrt{(1-\rho^2)}}\exp\left(-\frac{z}{2(l-\rho^2)}\right),$$

where $$z \equiv \frac{(\delta f_1 - \mu_1)^2}{\sigma_1^2} - \frac{2\rho(\delta f_1 - \mu_1)(\delta f_2 - \mu_2)}{\sigma_1\sigma_2} + \frac{(\delta f_2 - \mu_1)^2}{\sigma_2^2},$$

$\delta f_1$ and $\delta f_2$ are the normalized frequency shifts in the first and second modes, respectively, $\mu_1$ and $\mu_2$ are mean values for frequency fluctuations in the first and second modes, respectively, $\sigma_1$ and $\sigma_2$ are standard deviations of the first and second modes, respectively, and $\rho$ is the correlation coefficient between the frequency noise in the two modes.

In one embodiment, a $|\delta f_1/f_1|$, $|\delta f_2/f_2|$ plane is mapped onto a $(\delta m/M, a)$ plane and a JPDF for mass and position, $JPDF_{\delta m, a}(\delta m, a)$ is calculated.

In one embodiment, the JPDF is used to determine the probability distribution of mass using the following formula:

$$PDF_{\delta m}(\delta m) = \int_{a=0}^{a=0.5} JPDF_{\delta m, a}(\delta m, a)da.$$

In one embodiment, the JPDF is used to determine the probability distribution of position using the following formula:

$$PDF_a(a) = \int_{\delta m=0}^{\delta m=\infty} JPDF_{\delta m, a}(\delta m, a)d(\delta m).$$

In one embodiment, a frequency jump due to an analyte landing is represented by a displacement of a noise JPDF by a vector formed by the two frequency shifts.

In one embodiment, $JPDF_{\delta m, a}(\delta m, a) = |J| \times JPDF_{\delta f_1, \delta f_2}(h_1(\delta m, a), h_2(\delta m, a))$ where, $h_1(\delta m, a) = -\delta m\, \phi_1(a)^2/\alpha_1$ and $h_2(\delta m, a) = -\delta m\, \phi_2(a)^2/\alpha_2$, where $\phi_n(a)$ is the $n^{th}$ resonance mode shape at a landing position, $a$, with a normalization condition $\max(\phi_n(a))=1$, $\alpha_n$ is a numerical factor defined as $$\alpha_n = 2\int_{a=0}^{a=1} \phi_2(a)^2 da,$$

wherein $\alpha_n$ characterizes an effective mass, $M_{eff}^{(n)} = (\alpha_n/2)M_{total}$, for each mode; and $|J|$ is a positive determinant of the matrix:

$$|J| = abs\left(\frac{\partial h_1}{\partial(\delta m)}\frac{\partial h_2}{\partial a} - \frac{\partial h_2}{\partial(\delta m)}\frac{\partial h_1}{\partial 2}\right).$$

In one embodiment, mass and position are calculated from the JPDF according to the following formula:

$$JPDF_{\delta m, a}(\delta m, a) = |J| \times \frac{1}{2\pi\sigma_1\sigma_2\sqrt{(1-\rho^2)}}\exp\left(-\frac{\Gamma}{2(1-\rho^2)}\right)$$

where:

$$|J| = \frac{2\delta m}{\alpha_1\alpha_2}[\phi_1(a)\phi_2(a)]\left|\frac{\partial\phi_1}{\partial\eta}\right|_{\eta=a}\phi_2(a) - \frac{\partial\phi_2}{\partial\eta}\bigg|_{\eta=a}\phi_1(a)\right|,$$

and $$\Gamma = \frac{\left(\frac{\delta m\phi_1(a)^2}{\alpha_1} + \mu_1\right)^2}{\sigma_1^2} - \frac{2\rho\left(\frac{\delta m\phi_1(a)^2}{\alpha_1} + \mu_1\right)\left(\frac{\delta m\phi_2(a)^2}{\alpha_2} + \mu_2\right)}{\sigma_1\sigma_2} + \frac{\left(\frac{\delta m\phi_2(a)^2}{\alpha_2} + \mu_2\right)^2}{\sigma_2^2}.$$

In one embodiment, the method is performed at temperature of about 70K to about 140K.

In one embodiment, the frequency shift is a downshift.

In one embodiment, the method comprises delivering the analyte to the resonator prior to measuring the landing position and mass of the analyte.

In one embodiment, the delivering is performed by an electrospray ionization delivery system.

In one embodiment, the delivering is performed by a MALDI delivery system.

In one embodiment, the MALDI delivery system delivers one or more of positively charged, negatively charged, or neutral particles to the resonator.

In one embodiment, the mass of the analyte is about a few Daltons or more.

In one embodiment, the mass of the analyte is about 500 kDa or more.

In one embodiment, the mass of the analyte is in the MDa range.

In one embodiment, the adsorption is physisorption.

In one embodiment, the analyte is one or more of an individual molecule, a molecular complex, an isoform, or a nanoparticle.

In one embodiment, the at least two modes are phase locked.

In one embodiment, the landing position is measured only when the analyte adsorbs in the center 50% of the resonator.

In one embodiment, the resonator is a doubly-clamped beam, and analysis is restricted to one half of the beam's length.

In one embodiment, the resonator is a cantilever, and the measuring comprises transducing the cantilever into motion at at least a first frequency mode, a second frequency mode, and a third frequency mode and detecting the frequency shifts in the at least first, second, and third modes upon adsorption of the analyte.

In one embodiment, the measuring is performed in real-time.

In one embodiment, the analyte is in a complex mixture.

In one embodiment, the complex mixture comprises a plurality of analytes.

In one embodiment, the delivering is performed by a LIAD delivery system.

In one embodiment, the LIAD system delivers one or more neutral molecules to the resonator.

In one embodiment, the present invention relates to an apparatus for measuring a mass of a sample comprising: (i) a NEMS resonator arranged to receive the sample delivered to the resonator at a landing position, and (ii) a LIAD delivery system.

In one embodiment, changes in the frequency of vibration of the resonator indicate a magnitude of mass added to the resonator.

In one embodiment, the sample comprises one or more analytes.

In one embodiment, the present invention relates to a method of measuring the mass of at least one analyte comprising: delivering the analyte to a resonator with a LIAD delivery system, receiving the analyte onto a NEMS resonator at a landing position, and detecting a vibration frequency of the resonator to measure an absorbed mass of the analyte.

At least one advantage for at least one embodiment includes the ability to detect a single-molecule NEMS-MS in real-time, for example as a molecule lands on the device. At least one advantage for at least one embodiment includes increased speeds of mass detection. At least one advantage for at least one embodiment includes high sensitivity. At least one advantage of at least one embodiment includes acquisition of mass spectra assembled molecule-by-molecule as each discrete adsorption event occurs. At least one advantage for at least one embodiment includes the ability to use NEMS-MS to analyze complex mixtures in real-time. At least one advantage for at least one embodiment includes the ability to resolve neutral species. At least one advantage for at least one embodiment includes the ability to resolve analytes under physiological conditions. At least one advantage for at least one embodiment includes increased resolving power for large masses.

DETAILED DESCRIPTION

Figure 1:
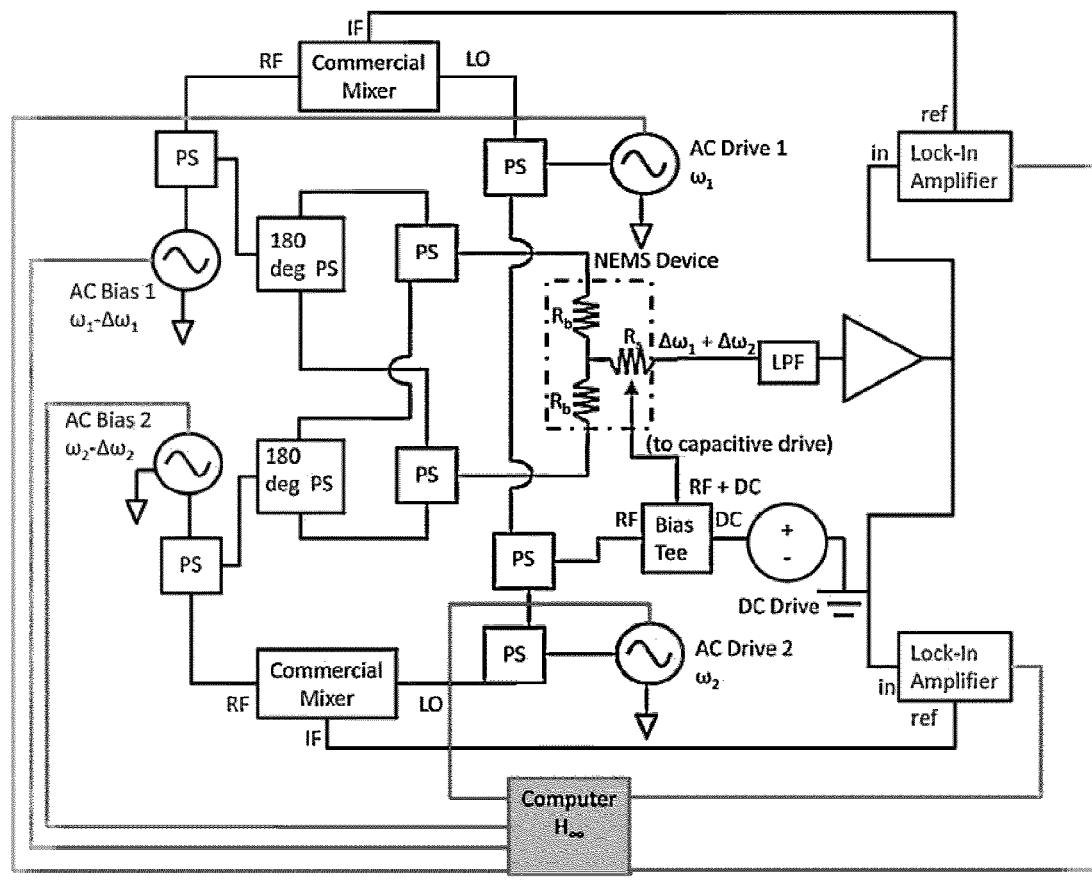
FIG. 1 is a diagram of a circuit suitable for actuation and readout of a NEMS resonator, where "PS" is a power splitter/combiner, "180 deg. PS" is a power splitter with 180° phase offset, "LPF" is a low pass filter, "in" is an input port of a lock-in amplifier, and "ref" is a reference port of a lock-in amplifier.

All references cited in this application are incorporated herein by reference in their entireties.

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

In some embodiments, the present disclosure relates to biological MS, for example with positive, negative, or neutral molecules. In some embodiments, the present disclosure relates to native MS, for example using near-physiological conditions. In some embodiments, the present disclosure relates to MS in the ultrahigh mass regime, for example about 1 MDa or higher. In some embodiments, the present disclosure relates to environmental dust counting and identification. In some embodiments, the present disclosure relates to nanoparticle studies, for example in nanotoxicology or material science. In some embodiments, the present disclosure relates to single organism and organic macromolecule detection, for example for exobiology studies. In some embodiments, the present disclosure relates to virus detection and identification through mass measurements. In some embodiments, the present disclosure relates to bacteriological population studies or single bacterium studies. In some embodiments, the present disclosure relates to studies of virus capsid assembly and maturation as monitored by NEMS MS. In some embodiments, the present disclosure relates to immunology studies through monitoring the changes in human antibody composition. In some embodiments, the present disclosure relates to imaging mass spectrometry with NEMS-MS detection.

The present disclosure relates to a NEMS-MS method of measuring a single analyte in real-time, where mass spectra can be assembled analyte-by-analyte is real-time, for example as each discrete adsorption event occurs. In some embodiments, the method comprises weighing individual molecules in real time, without the need to first collect an ensemble of identical particles. In some embodiments, for each arriving analyte, the mass and landing position can be determined by continuously tracking at least two simultaneously driven vibrational modes of a NEMS resonator. Discrete, time-correlated frequency shifts of these modes can resolve each molecular adsorption event as it occurs. Some embodiments of the present method employ NEMS-MS to analyze complex mixtures in real time, and can resolve the mass of each analyte of the complex mixture. In some embodiments, no assumptions about the sample mixture are made. In some embodiments, the complex mixture can comprise one or more analytes, e.g., about two or more, about 4 or more, about 10 or more, about 20 or more, about 100 or more, or about 1000 or more analytes.

In some embodiments, the analyte can comprise anything suitable for mass detection. For example, the analyte can comprise any small particle, such as one or more of an individual molecule, a molecular complex, an isoform, or a nanoparticle. In some embodiments, the analyte can be any particle with a mass that is about 10% or less, about 5% or less, or about 1% or less of the mass of the device. In some embodiments, the analyte can be any particle that has a mass of about 50 GDa or less, about 1 GDa or less, about 500 MDa or less, or about 1 MDa or less, about 1 kDa or less, or about 100 Da or less.

In some embodiments, the mass of the analyte can be about a few Daltons or more. In some embodiments, the mass of the analyte can be about 500 kDa or more. In some embodiments, the mass of the analyte can be in the MDa range or GDa range.

In some embodiments, a method comprises measuring a landing position and mass of at least one analyte adsorbed to a NEMS resonator by resolving adsorbate-induced frequency shifts in at least two modes, wherein during the resolving of the frequency shifts in the at least two modes, analysis is so that the transformation (G) from a fractional frequency shift pair to an analyte mass-position pair is one-to-one.

In some embodiments, the method comprises simultaneously tracking the resonance frequency of at least two modes of a NEMS resonator and then resolving the time-correlated, adsorption-induced frequency shifts in the at least two modes. In some embodiments, the induced frequency jumps in different modes occur simultaneously. In some embodiments, nominal values of mass and landing position can be resolved based on the simultaneous frequency shifts. In some embodiments, the frequency shifts in at least two modes are measured simultaneously.

Some embodiments also include an error analysis. For example, using a complete expression for mode shape can facilitate direct determination of the mass and position uncertainty of each arriving analyte.

NEMS Device for Mass Sensing

Some embodiments of the present invention relate to a device capable of measuring the mass and landing position of at least one analyte. In some embodiments, the device is a mass spectrometer. In some embodiments, the device comprises a resonator that can vibrate at a resonant frequency. In some embodiments, the resonant frequency can change in at least two modes when a small amount of mass is accreted on it. In some embodiments, the change in resonant frequency can be used to determine the total mass and landing position of the accretion.

The vibrational frequency of the resonator can be a sensitive function of its total mass. Any small variation in mass, e.g. from adsorbed analyte, can measurably alter the resonator resonant frequency.

Any resonator or device suitable to provide a mechanical response can be utilized in the present invention, such as a vibrational resonator, counter rotating or rotating resonator, torsional resonator, or compound resonator. For simplicity, all such potential devices will be hereafter referred to as "resonators".

In some embodiments, the resonator can be a beam, for example a doubly clamped beam.

In some embodiments, the resonator can be a cantilever.

The resonator can have physical properties suitable for detection of an analyte. For example, the resonator can be made of any suitable material such as such as inorganic materials, including semiconductor materials, such as Si, SiC, III-V and II-VI materials, insulating materials, such as metal or semiconductor oxides, nitrides or carbides, including SiN and $SiO_2$, glass and even organic materials, such as polymeric/plastic materials. Resonators can be made of pure metals or metal alloys. For example, the resonators may be made of pure metals that include, but are not limited to, copper, nickel, platinum, aluminum, chromium, tungsten, palladium, silver and gold. Resonators can also be made of metal alloys. Examples of such alloys include, but are not limited to, constantan, Karma, gold/palladium, and alloys based on the pure metals listed above. In some embodiments, resonators can be made of nanowires, carbon nanotubes, graphene or other two-dimensional materials, and fullerenes.

The resonator can be any suitable size, for example micron or nanometer sized. In some embodiments the resonator can have a length of about 1.6 to about 5 micrometers. In some embodiments, the resonator can have a width of about 800 nanometers to about 1.2 micrometers. In some embodiments, the resonator can have a thickness of about 10 nanometers to about 1 micrometer.

In some embodiments, the resonator can be a beam structure, such that one of the dimensions is more than five times the other two. In some embodiments, the beam can have a length of about 100 nm to about 100 micron, about 100 nm to about 1 micron, about 100 nm to about 500 nm, or about 200 nm to about 300 nm. In some embodiments, the beam can have transverse dimensions of about 20 nm to about 20 microns, or about 20 nm to about 200 nm, about 200 nm to about 100 nm, or about 20 nm to about 60 nm.

The resonator can be adapted to vibrate at a resonance frequency. In some embodiments, the resonator can be adapted to vibrate at about 1 MHz to about 1 GHz, for example at about 24 MHz. In some embodiments, the resonator can be adapted to vibrate at a resonance frequency when excited by an actuator.

The resonator can be adapted to vibrate in at least two modes, at least four modes, at least 5 modes, at least 10 modes, or at least 12 modes. In some embodiments, the resonator can be adapted to vibrate in the at least two modes simultaneously. In some embodiments, the at least two modes can be phase locked.

In some embodiments, the resonator can be adapted to vibrate in a first and a second mode. In some embodiments, the resonator can be adapted to vibrate in a first mode, a second mode, and a third mode.

Transduction of multiple modes can be accomplished by any suitable methods. For example, actuation in multiple modes can be achieved using proximal capacitive gates, wherein resonator motion is transduced using symmetric semiconducting piezoresistive strain gauges located near both ends of the device. In some embodiments, modes are transduced with at least one function generator. In some embodiments, each separate transduced mode is independently actuated with a separate at least one function generator. In some embodiments, power combiners and filters are used to transduce at least two modes simultaneously. In some embodiments, electrostatic electrodes can be used to transduce the at least two modes. In some embodiments, electrostatic electrodes can be located along the length of the resonator. In some embodiments the resonator can be actuated by an external piezoshaker crystal, thermo-optic forces, or optical gradient forces.

Detection can be by any suitable methods. For example, in some embodiments the resonator can be detected by optical interferometry methods or by magnetomotive detection. In some embodiments, the resonator can be detected by piezoresistive detection with downmixing or piezoresistive detection without downmixing. In some embodiments, the resonator can be detected by capacitive detection.

In some embodiments, a feedback loop can be implemented, for example by controlling electronic measurement instruments by a microprocessor or field-programmable gate array (FPGA) using a serial port, parallel port, General Purpose Interface Bus (GPIB), universal serial bus (USB), or any other kind of wired or wireless communication link.

In some embodiments, the NEMS resonator can be controlled and monitored using multimode readout circuitry. In some embodiments, the multimode readout circuitry can comprise a phase-locked loop (PLL). Non-limiting examples of the multimode readout circuitry are described in the working examples, and a diagram of one embodiment is shown in FIG. 1. In some embodiments of the multimode readout circuitry, power-combiners can be used to combine drive and bias signals for device actuation. In some embodiments, T-connectors, filters and lock-in amplifiers can be used to separate out a readout signal for device detection. In some embodiments, a simultaneous operation point of at least two modes can be found by performing two-dimensional resonance frequency sweeps on the at least two modes whereby the drive frequency of one mode is fixed while the at least one other mode is swept and after each sweep the constant mode gets incremented. In some embodiments, the frequency sweep can determine and correct the effects of mode-mode interaction in nanomechanical resonators. In some embodiments, the PLL timescales of both modes are kept close to each other so that single-molecule jumps happen in the same timescale.

In some embodiments, the NEMS device or NEMS resonator is maintained at reduced temperatures, for example about 70 K to about 140 K. In some embodiments, the device or resonator is cooled with a cryostat. The cryostat can cool the device with, for example, liquid Nitrogen or Helium. In some embodiments, the device can be kept at room temperature. Without being bound by theory, it is believed that keeping the device at room temperature is especially advantageous when measuring molecules that have large Van der Waals interactions with the device surface.

Device Fabrication

Devices and resonators of the present invention can be made by any suitable method. For example, the device can be fabricated using a top-down lithographic process using CMOS compatible materials. The device can be fabricated with nano-electronics state-of-the-art lithography and etching techniques. In some embodiments, the device can comprise a silicon-on-insulator (SOI) wafer, e.g., a about 100 nm to about 250 mm wafer, with a top silicon structural layer, e.g., a about 10 nm thick to about 500 nm-thick layer, and a buried oxide layer, e.g., a greater than 100 nm-thick, such as a 400 nm thick, buried oxide layer. In some embodiments, the top silicon layer can be implanted with boron ions (p-type) through a thin layer of thermal oxide. Homogeneous doping in the top silicon layer can be obtained through a specific annealing step, resulting in top layer resistivity of approximately 5 mΩ·cm to about 15 mΩ·cm, such as about 9 mΩ·cm. In some embodiments, the top silicon layer can be etched by anisotropic reactive ion etching (RIE).

A hybrid e-beam/DUV lithography technique (allowing 50 nm minimum feature size) can be used to define nano-resonators and electrode pads. The electrode pads can be any suitable material. For example, the electrode pads may be made of pure metals that include, but are not limited to, copper, nickel, platinum, aluminum, chromium, tungsten, palladium, silver and gold. Electrode pads can also be made of metal alloys. Examples of such alloys include, but are not limited to, constantan, Karma, gold/palladium, and alloys based on the pure metals listed above, such as gold-palladium. In some embodiments, the electrode pads are wirebond pads.

A metal layer, for example gold, copper, nickel, platinum, aluminum, chromium, tungsten, palladium, or silver can be used to connect the electrode pads to drive and readout electrodes. The electrodes can be made of any suitable material. For example, the electrodes may be made of pure metals that include, but are not limited to, copper, nickel, platinum, aluminum, chromium, tungsten, palladium, silver and gold. Electrodes can also be made of metal alloys. Examples of such alloys include, but are not limited to, constantan, Karma, gold/palladium, and alloys based on the pure metals listed above.

To decrease lead resistances, interconnecting leads can be made thicker with a AlSi layer, e.g., a 650 nm-thick layer, or any other metal suitable for the CMOS interconnections process. The nanoresonators can be released using a vapor HF isotropic etching to remove the sacrificial oxide layer beneath the structures. In some embodiments, the resonator can be defined by an etch mask, which can be made, for example, with chromium or strontium fluoride.

Figure 2A:
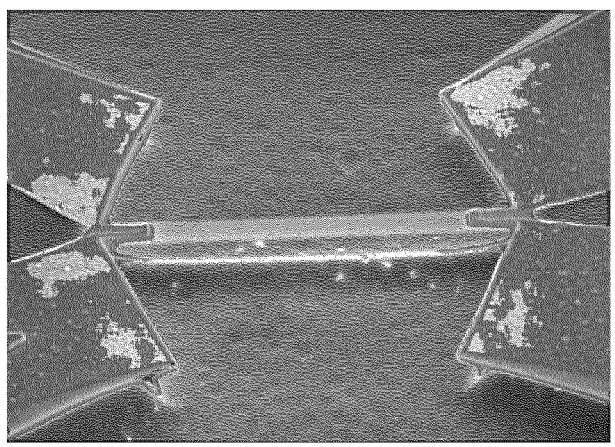
FIG. 2A is a scanning electron micrograph of a doubly-clamped beam NEMS resonator.
Figure 2B:
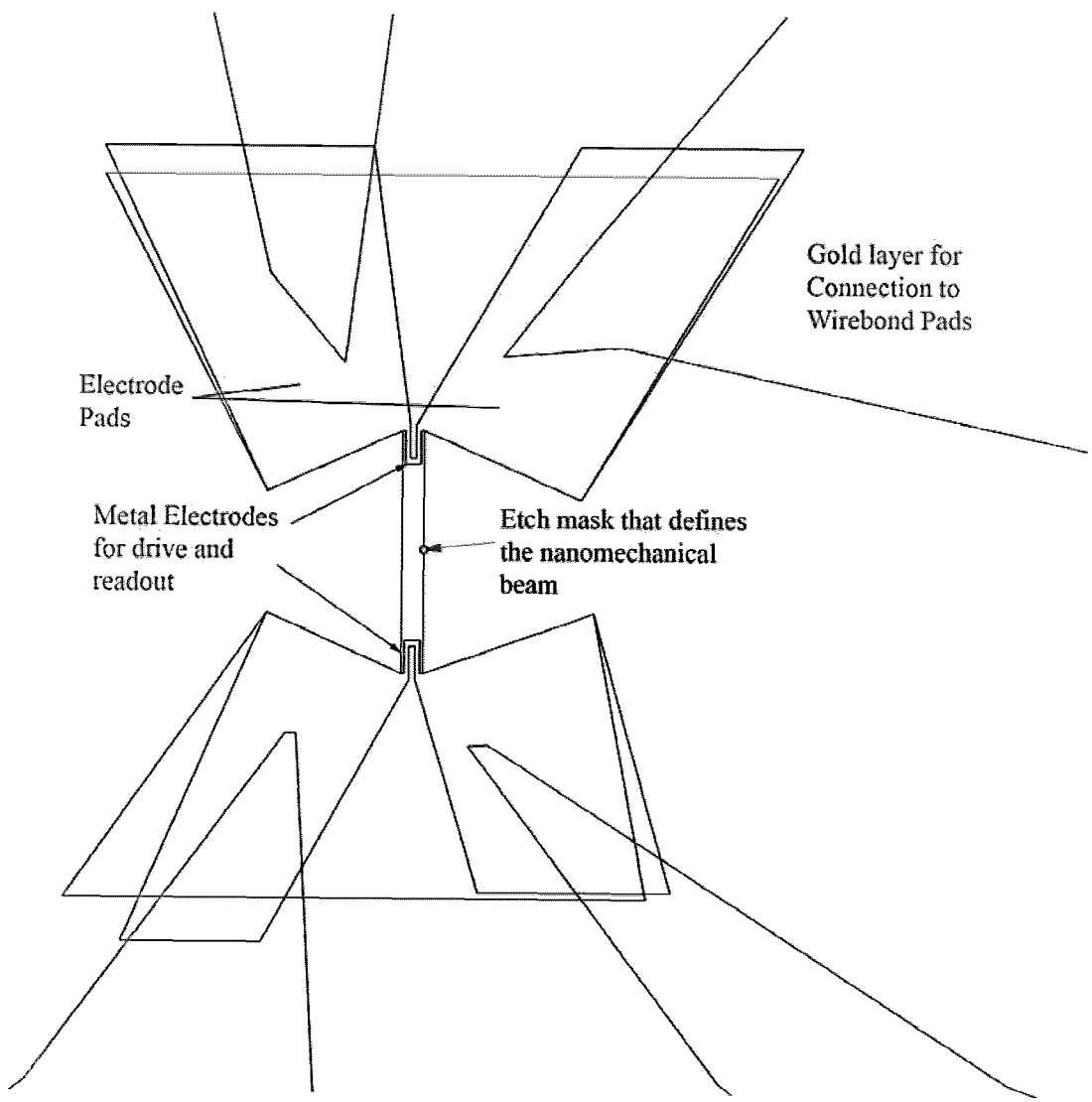
FIG. 2B is a diagram of a representative doubly-clamped resonator device.

In some embodiments, devices are fabricated as described in the working examples, e.g., working example 2. A colorized scanning electron micrograph of a representative doubly-clamped resonator device fabricated according to the working examples is shown in FIG. 2A. A diagram of a representative doubly-clamped resonator device is shown in FIG. 2B.

Delivery to NEMS Resonator

Analytes can be delivered to the resonators by any suitable methods, for example electrospray ionization (ESI), matrix assisted laser desorption ionization (MALDI), or laser-induced acoustic desorption (LIAD). ESI and MALDI have been described previously, for example in U.S. Pat. No. 8,227,747 and/or Cole, R. B., *Electrospray and MALDI Mass Spectrometry* (Wiley, 2010).

Briefly, ESI can convert the analytes in a solvent into ionized species in the gas phase. This can be accomplished by introducing the solution into a narrow needle kept at high voltage so as to induce Taylor instability at the tip of the liquid and form a spray with charged droplets. The charged droplets then experience cycles of rapid evaporation and Coulombic fission until all the solvent is evaporated and ionized analyte species are formed in the gas phase. In some embodiments, the ESI delivery system can comprise multiple stages of differential pumping to separate the resonator from the analyte solution, which can be at atmospheric pressure. In some embodiments, ESI can separate analytes leading to a low tendency for bunching or clumping of the analytes. In some embodiments, transport of analytes from the ESI device to the NEMS resonator requires guiding by ion optics.

Figure 3A:
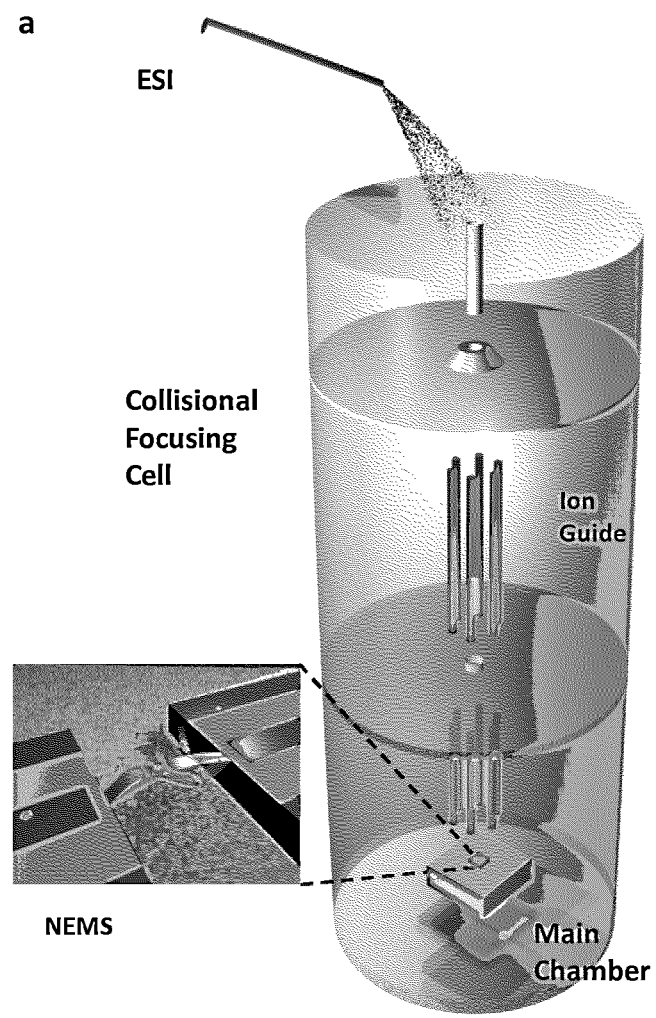
FIG. 3A shows a measurement setup for a three-chambered ESI delivery system for NEMS-MS.

In some embodiments, the ESI delivery system can comprise three chambers, as shown in FIG. 3A (not to scale). In some embodiments, additional chambers can be included to achieve a smaller pressure in the main chamber. For example, in some embodiments, four chambers can be used. In some embodiments, all chambers can be equipped with ion optics to guide the analytes.

ESI can create ionized analytes at, for example, atmospheric pressure. The ionized analytes can be transported into subsequent differential-vacuum stages. The first chamber can have a pressure of about 100 mTorr to about 362 Torr, for example about 1 Torr. The second chamber can have a pressure of about 1 mTorr to about 500 mTorr for example about 50 mTorr. The third chamber can have a pressure of about $10^{-7}$ Torr to about $10^{-4}$ Torr, for example about $10^{-5}$ Torr.

In some embodiments, the total flight path for the ions is about 0.2 m to about 2 m, for example about 0.5 m.

Figure 3B:
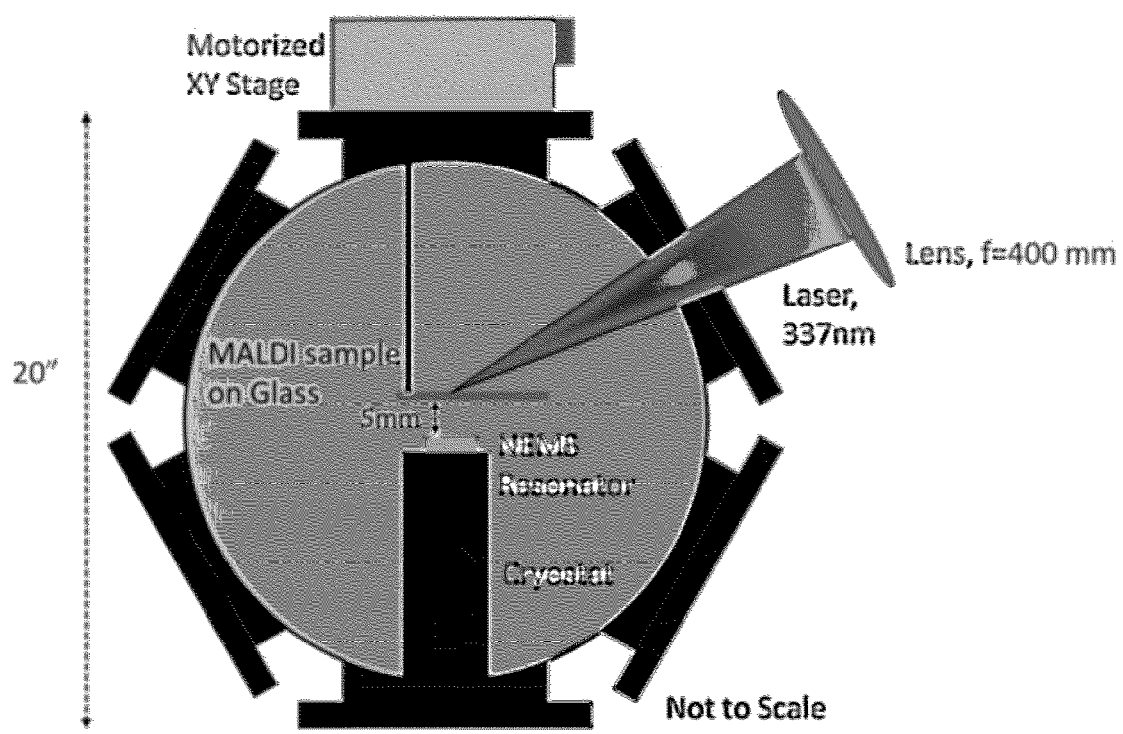
FIG. 3B shows a diagram of a MALDI delivery system for NEMS-MS.

MALDI can introduce samples in the solid phase with an external energy source (a laser) that, through absorption by a matrix chemical premixed with the analyte, both promotes the analytes to vapor phase and ionizes them. FIG. 3B shows a diagram of a MALDI experimental setup embodiment. MALDI typically forms analyte ions with smaller charge states than ESI. In some embodiments, solid phase analytes can be introduced in a vacuum chamber that, after introduction, requires no access to ambient conditions and thus allows for low pressure in the device region. In some embodiments, MALDI techniques require sample preparation beforehand, for example to avoid bunching of analytes when they are desorbed by the laser. Avoiding bunching of analytes can be accomplished by any known methods, such as addition of glycerol. In some embodiments, desorbed analytes have sufficient kinetic energy to reach the NEMS resonator without guidance by ion optics.

In general, the MALDI process relies on a compound, termed the matrix, which is used to efficiently absorb laser light and become ionized. The matrix can be mixed with the analyte so that when the matrix absorbs the laser light and is ionized, it in turn induces ionization in the analyte, bursting into a plume promoting both species into the gas phase. In some embodiments the analyte can act as a matrix, for example when the analyte is one or more nanoparticle, e.g., gold nanoparticles.

In some embodiments, Laser-Induced Acoustic Desorption (LIAD) can be used to deliver analytes to the resonator. LIAD can, for example, deliver neutral analytes to the resonator by using acoustic waves generated by a laser pulse in a thin metal foil. In some embodiments, LIAD is a background free technique.

Figure 3C:
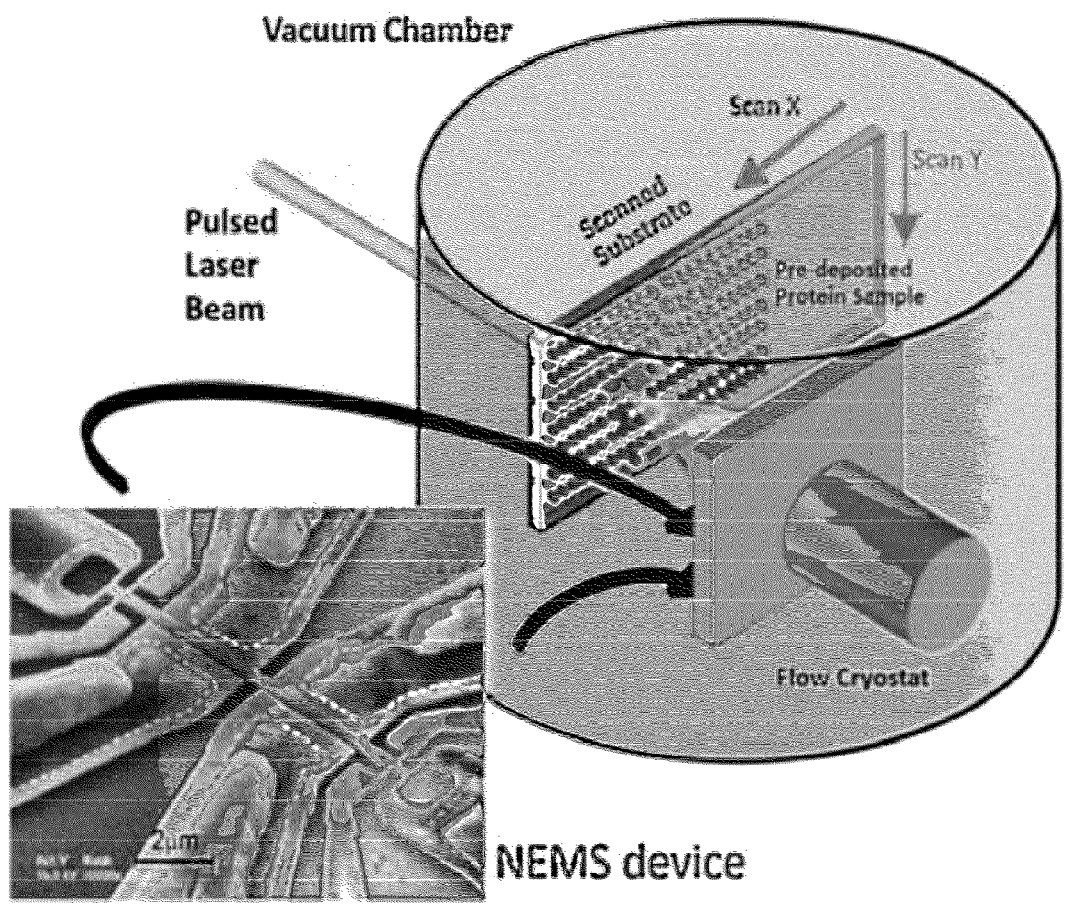
FIG. 3C shows a diagram of a LIAD delivery system for NEMS-MS.

In some embodiments, a LIAD sample with pre-deposited surface analytes can be inserted into a sample holder in a ultra-high-vacuum (UHV) chamber. In some embodiments, the NEMS device can be mounted at the end of a UHV flow cryostat. FIG. 3C shows a diagram of a LIAD experimental setup embodiment.

A laser spot can be aligned to the NEMS device using a transparent substrate. In some embodiments, the laser spot is pre-aligned. In some embodiments, the distance between the LIAD substrate and the NEMS device can be varied, for example from about 1 cm to about 5 cm. In some embodiments, the distance is fixed during an experiment, for example at about 2 cm to about 3 cm. In some embodiments, the laser is pulsed, for example at 1 Hz while the substrate is scanned in the X and Y directions.

In some embodiments, the laser frequency is slower than the inverse of the PLL time constant. The PLL time constant is not limited. If, for example, the PLL time constant is 0.5 s, then in some embodiments the laser frequency is less than about 2 Hz.

In some embodiments, each laser pulse can produce a plume of analyte material. In some embodiments, the plume is directed towards the device, and individual anayltes can randomly land on the device.

The LIAD substrate can be made of any suitable materials. For example, in some embodiments, the substrate can comprise one or more of a confining layer, an absorbing layer, and a substrate layer. In some embodiments, the analyte is deposited on the substrate layer.

Figure 3D:
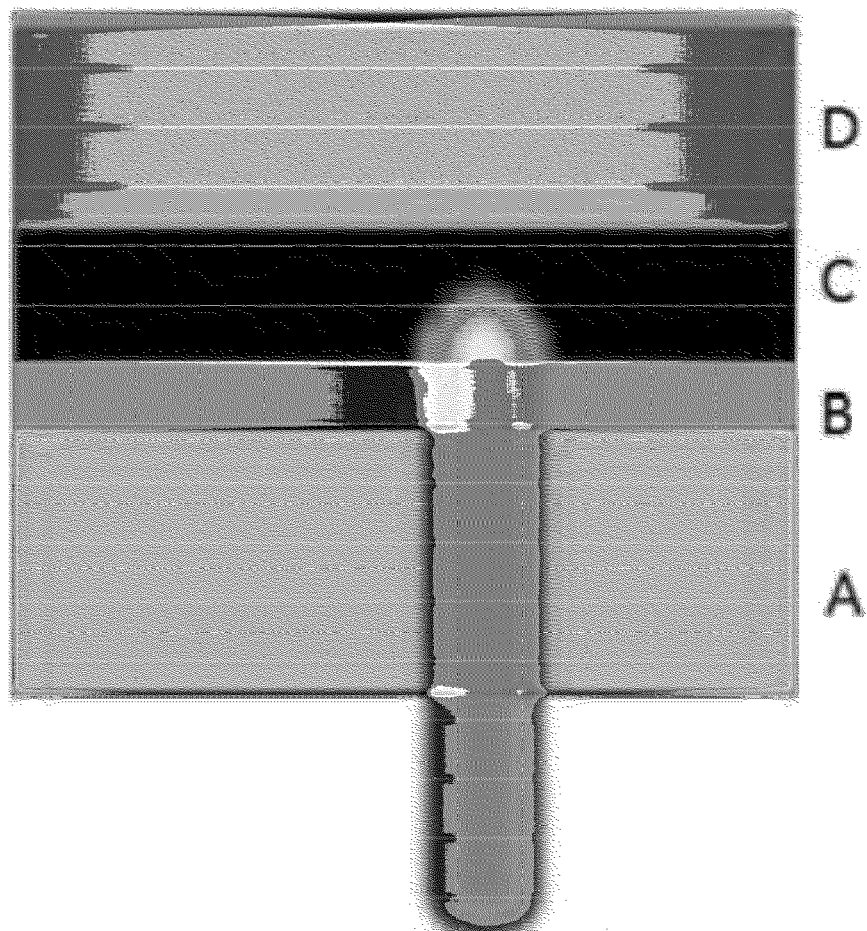
FIG. 3D shows a diagram of a LIAD substrate for use in NEMS-MS, where the vertical line represents a laser-emitted light.

In some embodiments, the substrate layer is deposited on the absorbing layer. In some embodiments, the absorbing layer is deposited on the confining layer. A diagram of a LIAD substrate can be seen, for example, in FIG. 3D. In some embodiments, the substrate layer is adhered to the absorbing layer with any suitable material, for example a glue. In some embodiments, the substrate layer is adhered to the absorbing layer with UHV epoxy.

Without being bound by theory, it is believed that the confining layer transmits laser light and focuses expansion towards the substrate layer. The confining layer can be about 500 microns to about 2 mm thick, for example about 1 mm thick. The confining layer can be made of any suitable material, for example any material that is transparent at the laser wavelength. In some embodiments, the confining layer can be glass. In some embodiments, the confining layer is a glass slide.

Also without being bound by theory, it is believed that the absorbing layer efficiently absorbs laser light. In some embodiments, the absorbing layer has high thermal expansion. For example, in some embodiments, the coefficient for thermal expansion is about 6 $\mu m \cdot m^{-1} \cdot K^{-1}$ or more, e.g., about 23.1 $\mu m \cdot m^{-} \cdot K^{-1}$. In some embodiments, the absorbing layer has a high Young's modulus, for example about 50 to about 200 GPa. In some embodiments, the absorbing layer can be about 50 microns to about 1 mm thick. The absorbing layer can be made of any suitable material, for example aluminum, silver, copper, gold, titanium, silicon, or any other solid semiconductor.

Also without being bound by theory, it is believed that the substrate layer can minimally attenuate a pressure pulse. In some embodiments, the substrate layer can insulate analytes from laser heat. In some embodiments, the substrate layer can be a metal, for example, titanium, aluminum, silver, copper, or gold, and can be about 5 to about 20 microns thick, or about 8 to about 15 microns thick, for example about 12 microns thick. In some embodiments, the substrate layer can be made of a solid semiconductor, for example silicon, and be up to 500 microns thick.

In some embodiments of the present invention, the charge state of the analyte is immaterial. The analyte can be, for example, positive, negative, or neutral. In some embodiments, the NEMS-MS is sensitive to only the inertial mass of the molecule and thus produces nominally the same mass spectra irrespective of the analyte delivery method or charge state of the analyte.

In some embodiments the analyte delivery is performed in a vacuum system. In some embodiments, the vacuum system is a table-top vacuum system. In some embodiments, the resonator can be in a high vacuum chamber. In some embodiments, the high vacuum chamber can have a pressure of about $10^{-11}$ to about $10^{-4}$, e.g., about $10^{-9}$ Torr.

Irrespective of the delivery method used, in some embodiments the analyte is accreted onto the resonator after delivery to the resonator. In some embodiments, the analyte adsorbs onto the resonator, for example through physisorption. In some embodiments, the analyte is delivered to a random position on the NEMS resonator.

Measuring Frequency Shifts in at least Two Modes

Measurement of frequency shifts in the NEMS resonator can be by any suitable method, for example by using high-frequency electronic components and a feedback loop as described in the working examples. In some embodiments, the measuring comprises resolving analyte-induced frequency shifts in at least two modes. In some embodiments, the analyte is adsorbed to the resonator, and the measuring comprises resolving adsorbate-induced frequency shifts in at least two modes.

In some embodiments, the frequency shift is measured in a first mode and a second mode. In some embodiments, the frequency shift is measured in a first mode, a second mode, and a third mode.

In some embodiments, the landing position and mass of an analyte is measured by resolving adsorbate-induced frequency shifts in at least two modes, wherein during the resolving of the frequency shifts analysis is so that the transformation (G) from the fractional frequency shift pair to the analyte mass-position pair is one-to one.

In some embodiments, adsorption of analytes onto the resonator can be modeled as that of point particles accreting instantaneously and rigidly upon the device. A point analyte with mass $\delta m$ can downshift the resonant frequency of a nanomechanical resonator with mass M in the following way:

$$\frac{\delta f_n}{f_n} = -\frac{\delta m}{M} \frac{\phi_n(a)^2}{\alpha_n} \quad (1)$$

where $f_n$ is the resonant frequency of the $n^{th}$ mode and $\delta f_n$ is the frequency shift for this mode. Examples of a time-correlated downshift of resonance frequency in a first mode and a second mode can be seen in FIGS. 4A-B. The fractional frequency shift, $(\delta f_n/f_n)$ is proportional to the fractional mass change, $(\delta m/M)$. $\phi_n$ denotes the mode shape for the $n^{th}$ mode, and a denotes the landing position of the molecule upon the beam. The numerical constant $\alpha_n$ is defined as:

$$\alpha_n = 2 \int_{a=0}^{a=1} \phi_n(a)^2 da \quad (2)$$

which characterizes the effective mass, $M_{eff}^{(n)} = (\alpha_n/2)M_{total}$, for each mode.

Figure 4A:
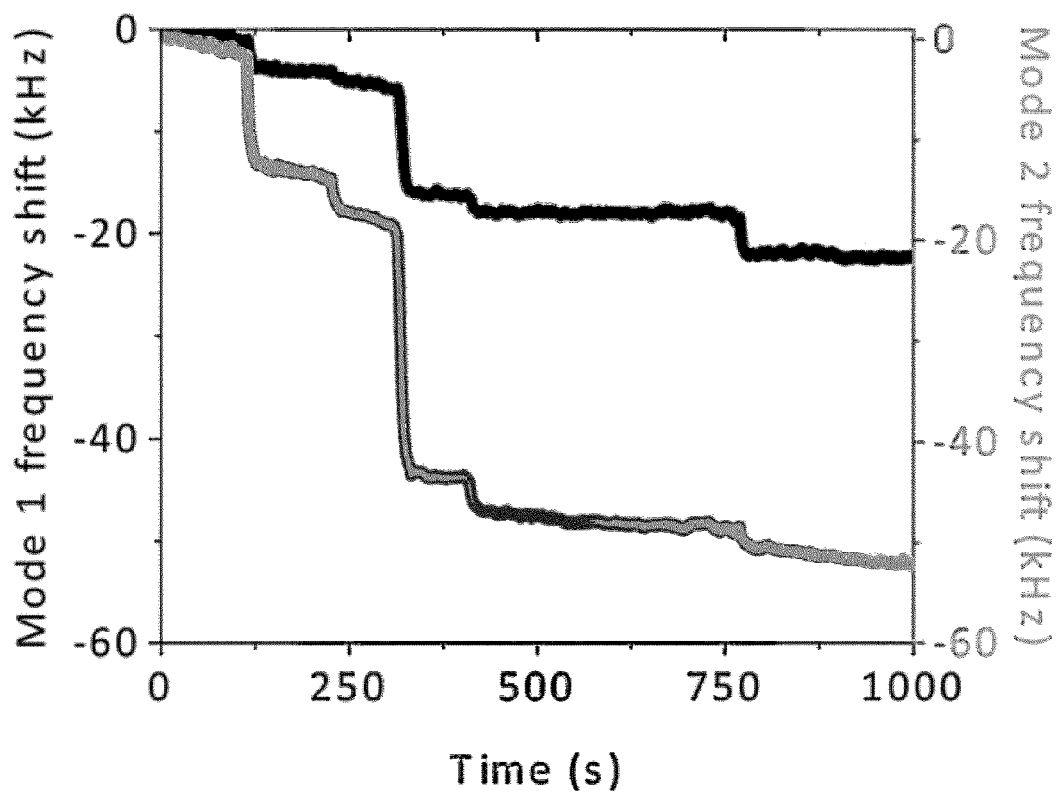
FIG. 4A shows time-correlated frequency shifts in mode 1 (black) and mode 2 (gray) corresponding to individual gold nanoparticles landing on a NEMS resonator.
Figure 4B:
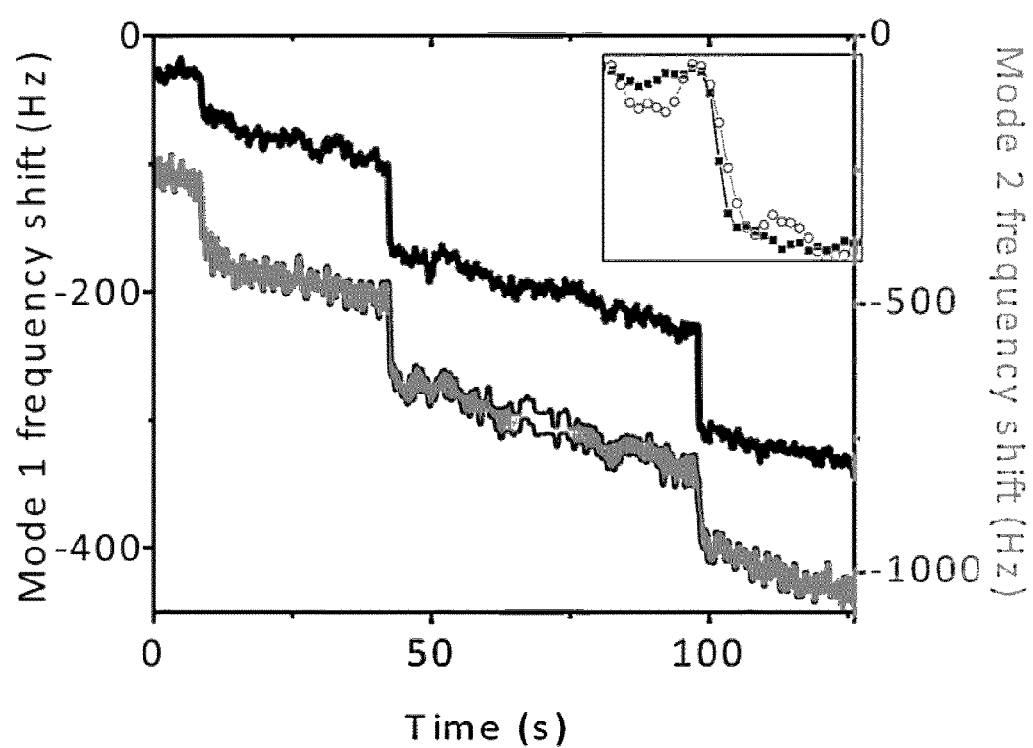
FIG. 4B shows time-correlated frequency shifts in mode 1 (black) and mode 2 (gray) corresponding to individual IgM molecules landing on a NEMS resonator; the inset shows an enlarged view of one of the frequency shifts.
Figure 4C:
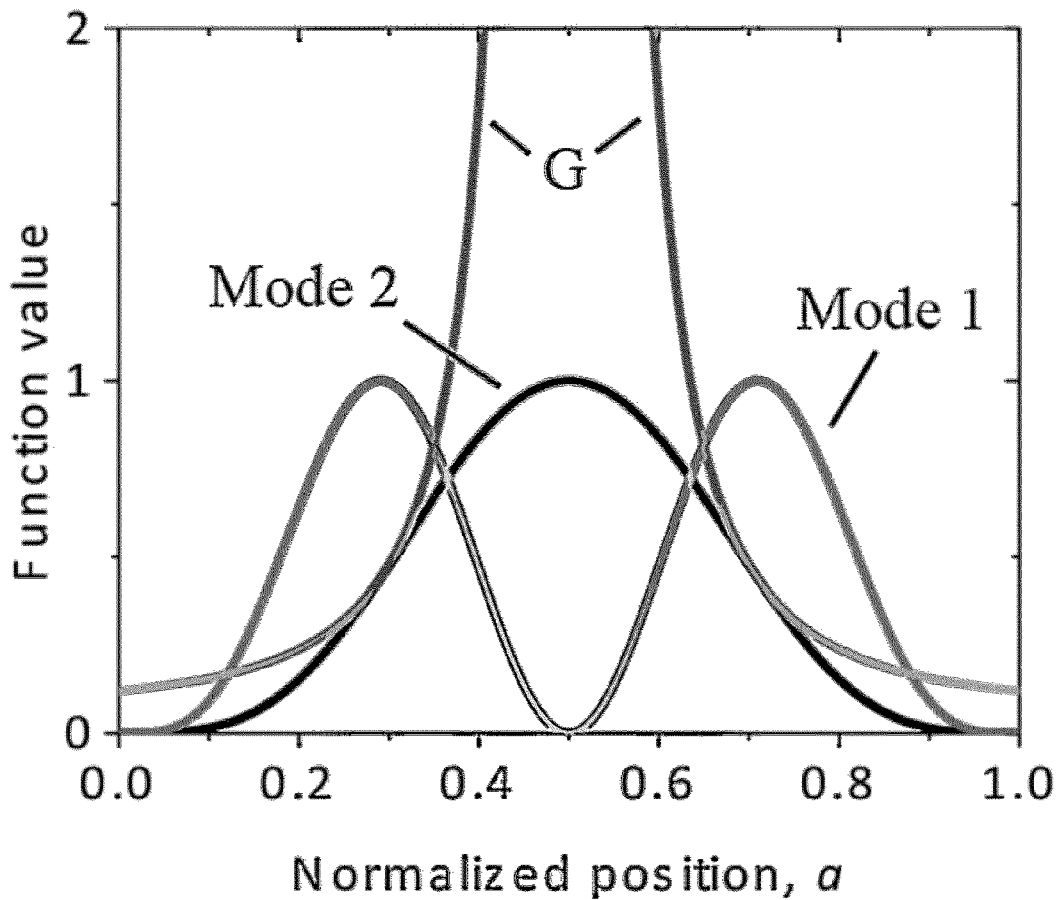
FIG. 4C shows responsivities of the first two modes of a doubly-clamped beam and the ratio of these responsivities, G.

For a symmetric NEMS doubly-clamped beam, for example, resolving the adsorbate-induced frequency shifts in at least the first two modes can determine the mass of the analyte and its position of adsorption. The mode shapes and the position-dependent responsivities of the first two modes are shown in FIG. 4C, along with the ratio of these responsivities, G. The ratio of the responsivities of two arbitrary modes, $$G(a) \equiv \frac{\phi_n(a)^2}{\phi_n(a)^2}$$

determines whether their simultaneous measurement is sufficient for real-time mass detection. If G is invertible, then a unique value for the position, and thus the mass of the molecule, can be obtained.

Even if G is not invertible, determination of mass and adsorption position can be measured if analysis is restricted so that the transformation from the fractional frequency shift pair to the analyte-position pair is one-to-one. For example, analysis can be restricted to one half of the resonator's length due to the inherent symmetry of a structure, such as when using a double-clamped beam.

Defining the normalized mass change as $\delta m \equiv \Delta m/M_{total}$ and the normalized frequency shift as $\delta f = (\Delta f/f_9)$, the first equation can be written as:

$$\delta m\, \phi_n(a)^2 = -\alpha_n \delta f_n. \quad (3)$$

Using the first two modes of the NEMS resonator, the above equation can be written as:

$$\frac{\phi_1(a)^2}{\phi_2(a)^2} = \frac{\alpha_1 \delta f_1}{\alpha_2 \delta f_2}. \quad (4)$$

As discussed above, for a doubly-clamped beam, the mass $\delta m$ and the position a can be determined from the first two modes of the NEMS resonator if the function, defined as:

$$G(a) \equiv \phi_1(a)^2/\phi_2(a)^2 \quad (5)$$

is invertible, i.e. if a single valued $G^{-1}[\delta f_1, \delta f_2]$ exists. In this case, position can be obtained by:

$$a = G^{-1}\left(\frac{\alpha_1 \delta f_1}{\alpha_2 \delta f_2}\right) \quad (6)$$

A smooth function is invertible if it is one-to-one and onto. For a doubly-clamped beam, the function G(a), as shown in FIG. 4C, is onto but is not a one-to-one function and thus cannot be used to evaluate a single value for the position, a.

However, because of the inherent symmetry of the doubly-clamped beam, the two position solutions for equation (3) are equidistant from the center of the beam:

$$\phi_1(a_1)^2 = \phi_1(a_2)^2 \quad (7)$$

$$\phi_2(a_1)^2 = \phi_2(a_2)^2 \quad (8)$$

and therefore the two solutions yield the same mass value:

$$\delta m = \frac{-\alpha_1 \delta f_1}{\phi_1(a_1)^2} \quad (9)$$

-continued $$= \frac{-\alpha_1 \delta f_1}{(\phi_1(G^{-1}[\delta f_1, \delta f_2]))^2}$$

While the above analysis is true for the first two modes of the doubly-clamped beam, an arbitrary choice of two modes of the doubly-clamped beam would not, in general, result in a single valued G even after accounting for the symmetry of the device. In some embodiments, it is therefore important to choose the appropriate modes or expand the analysis. For a cantilever, for example, the mass and position of the species landing on the NEMS resonator can be determined if at least the first three cantilever modes are used.

Resolving Single Mode Adsorbate-Induced Frequency Shifts

When a particle lands on the beam, an abrupt frequency shift can be measured. This measured frequency shift contains some amount of frequency noise that can degrade the measurement. In the ideal case of no noise, the frequency shift due to the landing event would be:

$$\Delta f_{ideal} = -\alpha \phi(a)^2 \delta m. \tag{10}$$

In the presence of noise, the measured value is:

$$\Delta f_{measured} = \Delta f_{ideal} + \tilde{f}_{noise}. \tag{11}$$

$\tilde{f}_{noise}$ denotes the frequency noise term in the measurement of which only a statistical description is available. The best estimate for the ideal frequency shift ($\Delta f_{estimated}$) is:

$$\Delta f_{estimated} = \Delta f_{measured} - \tilde{f}_{noise} \tag{12}$$

This estimate for the frequency jump can be treated as a random variable. Using the inverse probability theorem, this random variable is centered at the measured frequency jump and has the same statistical distribution as the frequency noise:

$$PDF_{jump}(\Delta f) = PDF_{noise}(\Delta f - \Delta f_{measured}). \tag{13}$$

$PDF_{jump}(\Delta f)$ denotes the probability distribution of the new statistical variable, the frequency jump, calculated for frequency change, $\Delta f$. $PDF_{noise}(\Delta f - \Delta f_{measured})$ denotes the probability distribution of the frequency noise calculated for the frequency change of $\Delta f - \Delta f_{measured}$. According to the above equation, a frequency shift can be represented statistically by translating the frequency noise PDF by the amount of the frequency shift. If the signal-to-noise ratio of the measurement is good, then this new random variable is sharply concentrated around the measured frequency shift.

Resolving Two-Mode Adsorbate-Induced Frequency Jumps

To account for the two statistical variables and their correlations, joint-probability density function formalism can be used, for example by using a bivariate Gaussian distribution. A joint Gaussian distribution for the frequency noise of the two modes can be described mathematically in the following form:

$$JPDF_{\delta f_1, \delta f_2}(\delta f_1, \delta f_2) = \frac{1}{2\pi\sigma_1\sigma_2\sqrt{(1-\rho^2)}} \exp\left(-\frac{z}{2(1-\rho^2)}\right) \tag{14}$$

where:

$$z \equiv \frac{(\delta f_1 - \mu_1)^2}{\sigma_1^2} - \frac{2\rho(\delta f_1 - \mu_1)(\delta f_2 - \mu_2)}{\sigma_1\sigma_2} + \frac{(\delta f_2 - \mu_1)^2}{\sigma_2^2}. \tag{15}$$

$\delta f_1$ and $\delta f_2$ represent the normalized frequency shifts in the first and second modes, respectively. $\mu_1$ and $\mu_2$ are the mean values for frequency fluctuations in the first and second modes, respectively, which can be negligible if the frequency of the resonator does not drift strongly. $\sigma_1$ and $\sigma_2$ represent the standard deviations of the two modes, respectively. $\rho$ is the correlation coefficient between the frequency noise in the two modes.

After modeling the two-mode frequency noise with the JPDF formalism above, the measured frequency jumps can be represented in a similar way to the single mode case. A frequency jump due to a particle landing can be represented by a displacement of the noise JPDF by the vector formed by the two frequency shifts. After measuring frequency shifts $\delta f_1'$ and $\delta f_2'$ the JPDF describing the event has the same form as equation (15) with the appropriate substitutions.

For multimode measurements, the frequency noise statistics for the separate modes can be combined into a joint probability density function (JPDF) representation, $$JPDF_{\frac{\delta f_1}{f_1}, \frac{\delta f_2}{f_2}}\left(\frac{\delta f_1}{f_1}, \frac{\delta f_2}{f_2}\right) \tag{16}$$

Using a bivariate PDF transformation, $$\left|\frac{\delta f_1}{f_1}\right|, \left|\frac{\delta f_2}{f_2}\right|$$

the plane can be mapped onto the $$\frac{\delta m}{M},$$

a plane and a joint-PDF for mass and position, $JPDF_{\delta m, a}(\delta m, a)$, can be calculated.

The JPDF of each analyte in the multimode space describes an elliptically-shaped distribution, with the length of the principal axes corresponding to mass and position uncertainties. This two-dimensional JPDF can be projected onto either the mass or the position axis to determine the probability distribution of mass or position respectively:

$$PDF_{\delta m}(\delta m) = \int_{a=0}^{a=0.5} JPDF_{\delta m, a}(\delta m, a)da \tag{17}$$

$$PDF_a(a) = \int_{\delta m=0}^{\delta m=\infty} JPDF_{\delta m, a}(\delta m, a)d(\delta m) \tag{18}$$

These noise-transformation relations can be used to systematically analyze the performance of NEMS-MS experiments. For example, mass resolution as a function of analyte landing position can be obtained.

In some embodiments, analytes with smaller masses produce smaller relative frequency shifts and, in the presence of a fixed amount of frequency noise, will appear as a larger position uncertainty. Surprisingly, the position uncertainty can decrease for heavier species while the mass uncertainty remains constant. Without being bound by theory, it is believed that this is because mass resolution depends on the minimum resolvable frequency shifts, which remains constant due to the frequency noise regardless of the magnitude of the actual shifts from the arriving analytes. Position resolution, on the other hand, depends on the minimum resolvable angle in the $$\left(\frac{\delta f_1}{f_1}, \frac{\delta f_2}{f_2}\right)$$

plane, and improves as the magnitude of the frequency shifts become larger.

Figure 5:
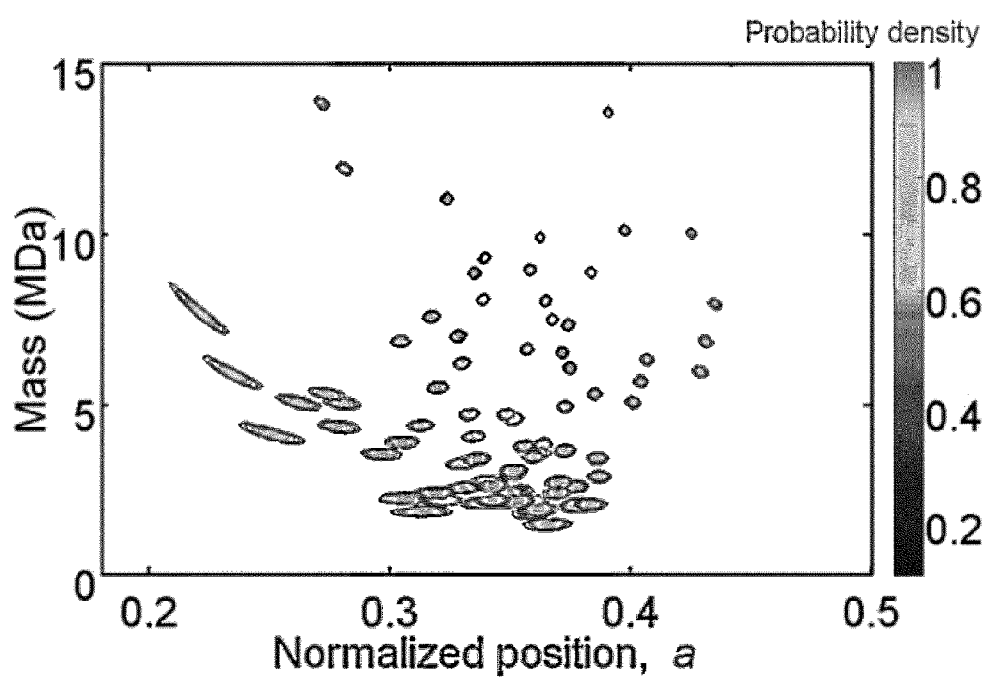
FIG. 5 shows experimental data from a MALDI NEMS-MS experiment with 5 nm gold nanoparticles, where each analyte captured by the resonator has an error disk that reveals its uncertainty in its mass and landing position on the resonator.

In some embodiments, each single adsorption event can be resolved with its own uncertainty level, as seen for example in FIG. 5, thereby giving rise to an apparent smoothness of the mass spectra for the individual analytes.

Transformation from Frequency Shift Domain to Mass-Position Domain

Figure 4D:
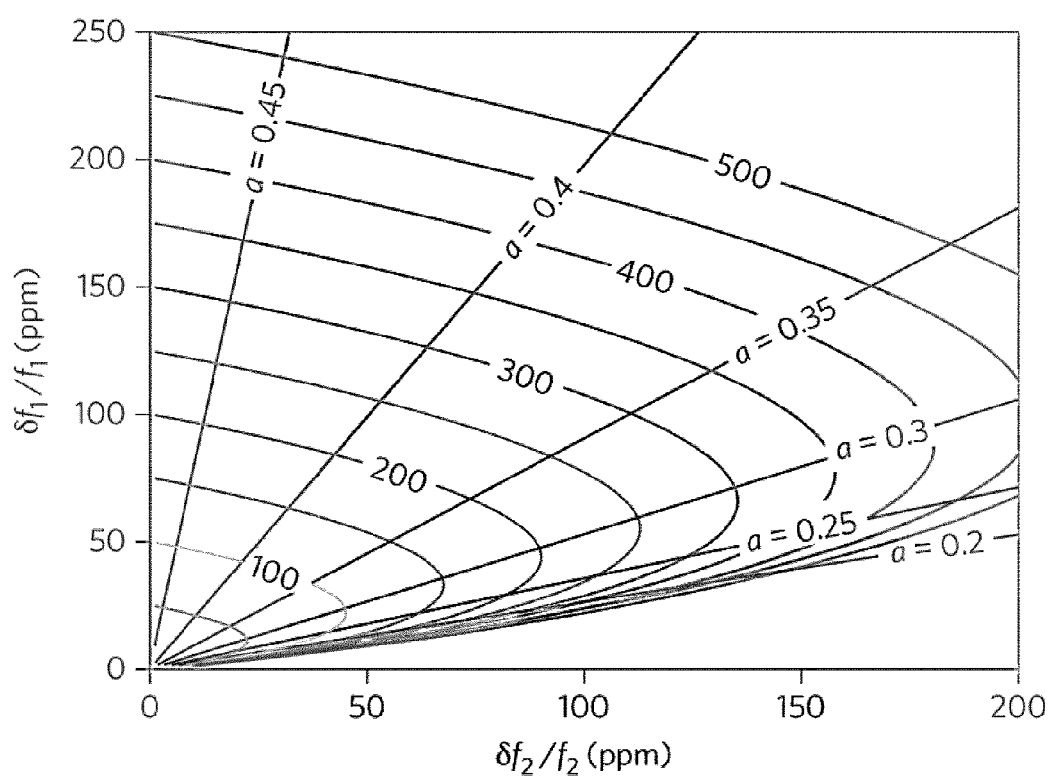
FIG. 4D graphically represents the transformation of experimentally observed, time-correlated frequency jumps from the first two modes of a doubly clamped beam into mass and landing position for each arriving analyte.

For a given frequency jump, we can obtain $\text{JPDF}_{\delta f_1, \delta f_2}(\delta f_1, \delta f_2)$. These two variables, $\delta f_1$ and $\delta f_2$, can be mapped onto two variables for mass ($\delta m$) and position (a). FIG. 4D graphically represents the transformation of experimentally observed, time-correlated frequency jumps from the first two modes of a doubly clamped beam into mass and landing position for each arriving analyte, where the x and y axes represent the measured fractional frequency jumps, scaled in parts per million (ppm). In the figure, straight lines passing through the origin denote constant-adsorbate-position values, where the beam center (a=0.5) corresponds to the y-axis. Elliptical curves represent contours for constant adsorbate mass, and are labeled in units of $m_p/M$ and scaled in ppm. The parametric curves in FIG. 4D hold only the first two same-plane modes of a doubly-clamped beam and assume only Euler-Bernoulli beam theory.

Figure 6A:
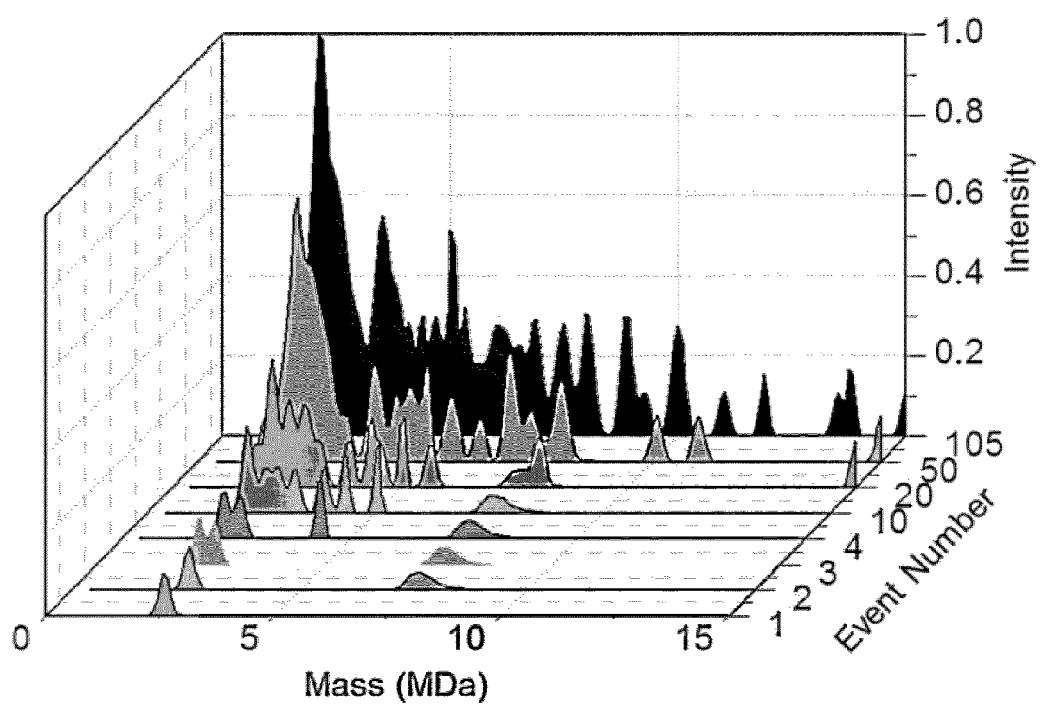
FIG. 6A shows a mass spectrum of 5 nm gold nanoparticles with glycerol as they arrive sequentially on a NEMS resonator, and where the total cumulative spectrum (black, at back) is the additive result of 105 individually measured particles.
Figure 6B:
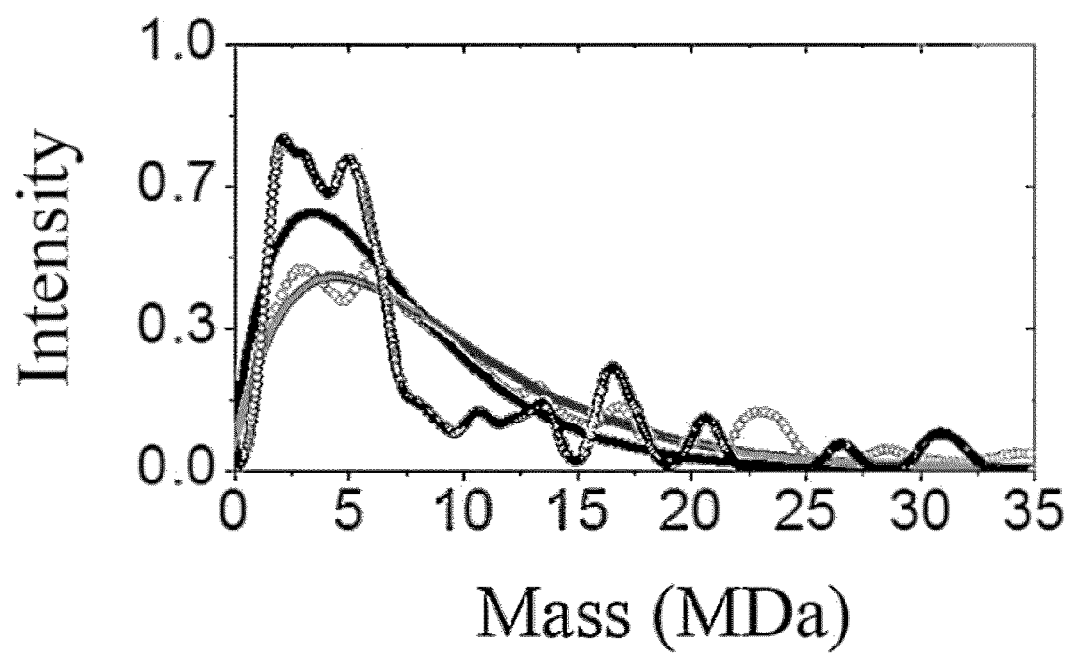
FIG. 6B shows mass spectra of 10 nm gold nanoparticles from ESI (gray, open circles) and MALDI (black, open circles) setups along with best fits to the data with both ESI (gray, solid line) and MALDI (black, solid line).
Figure 6C:
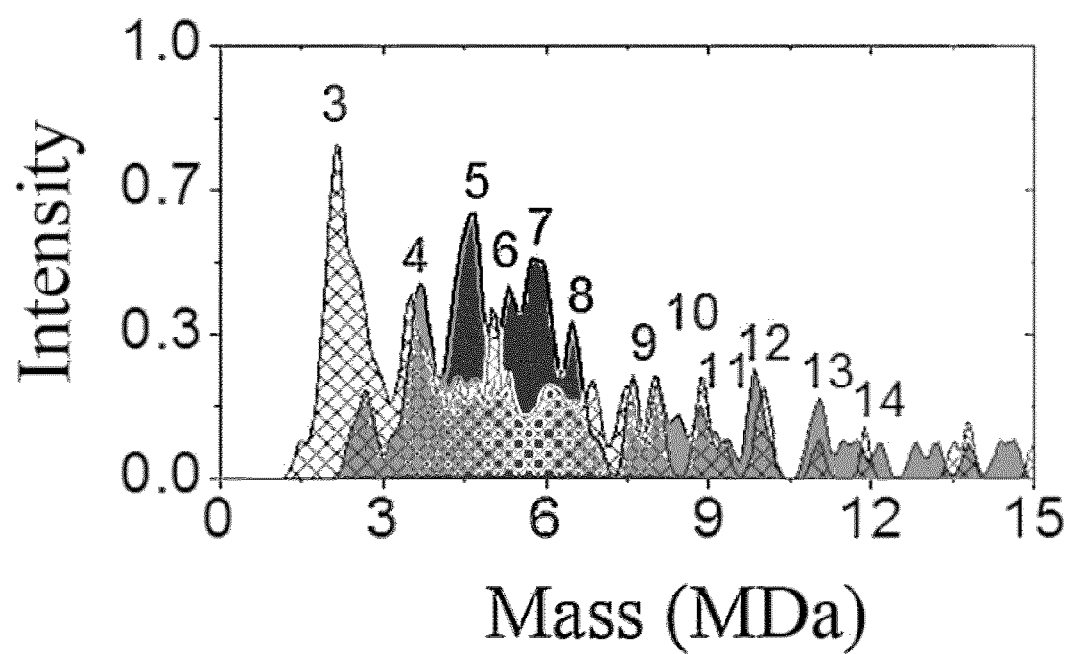
FIG. 6C shows mass spectra of 5 nm gold nanoparticles prepared with glycerol (patterned spectrum) and without glycerol (solid spectrum).

In some embodiments, each single adsorption event can be represented in the mass-position plane as a continuous probability distribution. In some embodiments, the mass spectrum can be represented by Gaussian-like distributions of accreted analytes where the width is dependent on the specific mass and position of the analyte. In some embodiments, each individual landing event can be represented in the mass spectrum, as shown for example in FIG. 6A and FIG. 6D. In some embodiments, as shown in FIG. 6E, decomposition of a spectrum into different polymerization levels can provide information about the relative and absolute presence of different analyte isoforms.

In some embodiments, the representation on the mass-position plane of the individual analytes can be added to generate a composite spectrum, as can be seen in FIGS. 6A-G. In some embodiments, only the center of the mass distribution is represented.

The joint-PDF for mass and position, $\text{JPDF}_{\delta m, a}(\delta m, a)$, can be calculated using the bivariate PDF transformation given by:

$$\text{JPDF}_{\delta m, a}(\delta m, a) = |J| \times \text{JPDF}_{\delta f_1, \delta f_2}(h_1(\delta m, a), h_2(\delta m, a)) \quad (19)$$

where $h_1(\delta m, a)$ and $h_2(\delta m, a)$ are the functional forms for $\delta f_1$ and $\delta f_2$, respectively (e.g., $\delta f_1 = h_1(\delta m, a)$). Thus, from equation (3) we have: $h_1(\delta m, a) = -\delta m \, \phi_1(a)^2/\alpha_1$ and $h_2(\delta m, a) = -\delta m \, \phi_2(a)^2/\alpha_2$. J denotes the Jacobian matrix, and $|J|$ is the positive determinant of the matrix:

$$|J| = \text{abs}\left(\frac{\partial h_1}{\partial(\delta m)}\frac{\partial h_2}{\partial a} - \frac{\partial h_2}{\partial(\delta m)}\frac{\partial h_1}{\partial a}\right). \quad (20)$$

Using this formalism and previous results for the PDF of the frequency shifts, the joint-PDF for the mass and position can be calculated:

$$\text{JPDF}_{\delta m, a}(\delta m, a) = |J| \times \frac{1}{2\pi\sigma_1\sigma_2\sqrt{(1-\rho^2)}} \exp\left(-\frac{\Gamma}{2(1-\rho^2)}\right) \quad (21)$$

with the positive determinant of the Jacobian explicitly written as:

$$|J| = \frac{2\delta m}{\alpha_1\alpha_2}[\phi_1(a)\phi_2(a)]\left|\frac{\partial\phi_1}{\partial\eta}\right|_{\eta=a}\phi_2(a) - \left.\frac{\partial\phi_2}{\partial\eta}\right|_{\eta=a}\phi_1(a)\right| \quad (22)$$

and the term in the exponential given as:

$$\Gamma = \frac{\left(\frac{\delta m\phi_1(a)^2}{\alpha_1} + \mu_1\right)^2}{\sigma_1^2} - \frac{2\rho\left(\frac{\delta m\phi_1(a)^2}{\alpha_1} + \mu_1\right)\left(\frac{\delta m\phi_2(a)^2}{\alpha_2} + \mu_2\right)}{\sigma_1\sigma_2} + \frac{\left(\frac{\delta m\phi_2(a)^2}{\alpha_2} + \mu_2\right)^2}{\sigma_2^2} \quad (23)$$

where all terms are as previously defined.

Modeling of Frequency Noise as Random Variables

Standard deviation can be used to characterize the dispersion of a statistical variable. However, for frequency measurements standard deviation can be a poor measure for quantifying dispersion because it depends on the sample size (N) and does not converge for certain types of frequency noise, for example flicker noise and drift (random walk noise).

In some embodiments of the present invention, an Allan deviation can be used to characterize the frequency noise. To calculate the Allan deviation, we first consider the fractional frequency difference, y[n], for each discrete time index, n:

$$y[n] = \frac{f[n] - f_0}{f_0} \quad (24)$$

where $f_0$ is the nominal frequency of the resonator and f[n] is the measured frequency of the NEMS resonator at the time step [n]. With this convention, the Allan variance $\sigma^2_{Allan}$ is defined as:

$$\sigma^2_{Allan} \equiv \frac{1}{2(N-1)}\sum_{n=1}^{n=N-1}(y[n+1] - y[n])^2, \quad (25)$$

where the Allan deviation is the square root of this quantity.

The frequency stability of a resonator can also depend on the time scale over which it is observed. For example, a resonator can be stable for short periods of time, but it may drift appreciably when observed over longer time scales. This kind of dependence on timescale can be reflected by the Allan deviation. The definition of the Allan deviation shown above is calculated for the fastest time scale, i.e. the sampling bandwidth, of the measurement. To calculate the Allan deviation over longer timescales, the data is sliced into time segments, each having the size of the relevant physical timescale. The average of each segment can be determined, and the Allan deviation for an ensemble composed of these averaged values can be calculated. For example, if the timescale of interest is $\tau$, such that $\tau = qT_{sampling}$, with q being some integer, then:

$$\sigma^2_{Allan}(\tau) = \frac{1}{2(M-1)} \sum_{m=1}^{M} (\overline{y[m+1]} - \overline{y[m]})^2. \quad (26)$$

$\overline{y[m]}$ is the average value of the fractional frequency difference, during the time interval denoted by m. Also, $$M = \frac{N}{q},$$

since we slice a total of N data points into segments containing q data points.

While the Allan deviation is a scalar parameter that characterizes the frequency noise, it does not contain a representation of all characteristics about the random fluctuations. In some embodiments, additional information about random fluctuations can be provided by defining a probability density function (PDF) for the frequency noise. The PDF of the frequency noise can be estimated from the experimental data. After measuring the fractional frequency difference, y[n], the resulting ensemble can be fit within a typical PDF model. This can be done, for example, with a Gaussian distribution that models the frequency noise sufficiently well. The variance in the Gaussian distribution can have a value similar to the Allan variance because both parameters quantify the dispersion of the NEMS frequency.

Noise Transformations

Noise-transformation relations can be used to systematically analyze the effect of various parameters, such as mass resolution, frequency stability, and correlation of noise, on the performance of mass spectrometry experiments.

For example, when two modes have similar noise performance, optimal mass resolution can be achieved for molecules landing on the points of maximum deflection for either mode. In some embodiments of the present invention, molecules arrive randomly along the length of the resonator and the mass spectra are then assembled piece-wise at the single molecule level. The mass measurement for events at either end of the device can contribute to a larger error in the mass and effectively degrade the mass resolution. To prevent this adverse influence on mass resolution, in some embodiments only the mass data obtained from a sensitive part of the NEMS is used for obtaining measurements. For example, the mass resolution is almost constant for the center 50% of the beam (0.25≤a≤0.50). In some embodiments, the optimal operational region of the NEMS beam is the center 50%. In some embodiments, experimental analysis is performed on frequency shift events such that a≥0.25. In some embodiments, higher modes can be used to extend the useful area of the beam.

In some embodiments, the noise in the higher modes can be larger than that observed in the lower modes and use of higher modes can therefore affect mass resolution. If symmetrical modes are used, then the fundamental in-plane and out-of-plane modes and the mass resolution is symmetrical with respect to the interchange of these modes due to their geometric equivalence. If modes with different shapes are used, the geometric difference manifests itself in the mass resolution plot, and sweet spots can emerge near the anti-nodes of these modes. For example, when two modes have similar Allan variances, the mass resolution can almost be constant in the center 40% of the beam. As one of the modes becomes noisier, the region of the beam closer to the anti-node of the noisy mode can become less responsive. This can have a significant effect on the capture cross-section as well as the effective mass resolution in mass spectrometry measurements.

For uncorrelated noise statistics the mass resolution can stay fairly constant for the center 50% of the beam. As the correlation increases, the degrading effects can predominantly be observed at positions where the mode displacement of both the modes is significant. A correlated noise in the two modes can thus affect the effective mass resolution adversely and is therefore undesirable.

Additional non-limiting embodiments are described in the below working examples.

WORKING EXAMPLES

NEMS-MS with ESI delivery was performed with human IgM and with 10 nm gold nanoparticles (GNPs). NEMS-MS with MALDI delivery was performed with 5 nm and 10 nm GNPs. NEMS-MS with LIAD delivery was performed with IgM, thyroglobulin, apoferritin, proteasome, 70s ribosome, and RAG complex.

Example 1

Sample Preparation

Human IgM solution was purchased from Sigma-Aldrich. Colloidal GNPs with nominal diameters of 5 nm (mean diameter=5.1 nm, variance=19%) and 10 nm (mean diameter=10.7 nm, variance=10%) were also purchased from Sigma-Aldrich.

For LIAD NEMS-MS measurements, IgM, thyroglobulin, and apoferritin were purchased from Sigma-Aldrich. Proteasomes, ribosomes, and RAG proteins were prepared in the laboratory.

ESI Samples

NEMS-MS experiments were performed with human IgM and GNPs. Human IgM solution was buffer exchanged to 200 mM aqueous ammonium acetate, with a final antibody concentration of approximately 1 mg/mL prior to introduction into the ESI needle.

10 nm colloidal GNPs samples were diluted by equal amounts of methanol prior to introduction into the ESI needle.

MALDI Samples

MALDI sample plates were prepared by washing the stock colloid GNP solutions in water and, using a centrifuge, concentrating the solutions to ~$5 \times 10^{14}$ particles/ml and $1 \times 10^{14}$ particles/ml for the 5 and 10 nm GNP samples, respectively. For some solutions, 10% glycerol (Sigma-Aldrich) in $H_2O$ was added. For each sample, 38 µl of solution was drip-dried onto 3 mm diameter spots on a pyrex sample plate. More specifically, the solution was deposited as 2.5 µl drops onto the sample plate, with fifteen drops per application (per spot). The deposited solution was dried between depositions, thereby maximizing particle surface density to obtain maximal flux from the MALDI process.

LIAD Samples

For LIAD-based experiments, the sample substrate was fabricated as follows. Ti foil (12.7 µm thick) was commercially bought from Alfa Aeser. It was cleaned with acetone, isopropyl alcogol, methanol, and UV ozone. The backside was covered with 500 nm of Aluminum using magnetron sputtering. UHV expoxy (Stycast 1266, Emerson and Cumings) was used to glue a standard microscope glass slide (0.5 µm thick, Fisher scientific) to the foil. After curing, proteins samples were deposited on the front side of the substrate prior to insertion into a vacuum apparatus.

To prepare protein samples, proteins were mixed (if in powder form) or buffer exchange (with a centrifuge) into ~1-2 µM solution of de-ionized water with 10-100 mM Ammonium acetate solution (Sigma Aldrich). Ribosomes were suspended in 10 mM magnesium acetate solution (Sigma Aldrich). Liquid samples were deposited onto prepared LIAD substrate stacks using either electro-spray deposition or pipetting and drying in ambient conditions. The electro-spray deposition consisted of a 100 micron diameter needle, charged to 4 kV. The solution was pushed through the needle using a syring pump at rates of 0.5-5 microleters/min. Total volume sprayed was ~500 microleter for 1 cm$^2$ substrate samples. For pipetting, 200 ul of sample solution was pipetted onto a 1 cm$^2$ substrate sample. Samples were immediately inserted into the vacuum chamber after drying. Drying was ~5 minutes for electro-spray deposition and ~30 minutes for pipetting.

Example 2

Device Fabrication

A NEMS resonator, as shown in FIG. 2A, was used in the GNP measurements with ESI delivery. Fabrication of the device has been described previously in Bargatin et al., 90 *Applied Physics Letters* 093116 (2007). Briefly, 100 nm low-stress silicon nitride on silicon wafers was used. Gold electrodes were fabricated symmetrically at the two edges defining the NEMS resonators using e-beam lithography and thermal evaporation. SrF$_2$ was subsequently deposited as an etch mask, again using e-beam lithography and thermal evaporation. The devices were suspended using anisotropic and isotropic plasma etching. The etch mask was removed by dipping the chip into HCl.

For MALDI-based experiments, ESI-based experiments with human IgM, and LIAD-based experiments, the device was fabricated according to previously published protocols. See Mile, 21 *Nanotechnology* 165504 (2010).

Example 3

ESI NEMS-MS

NEMS-MS experiments employing ESI delivery were carried out on a table-top vacuum system equipped with a flow cryostat. The flow cryostat was used to cool down a sample stage, on which a NEMS resonator was mounted, within a high vacuum chamber. For GNP samples, the device was operated at 70K, and for IgM samples the device was operated at 140K.

The ESI setup, as shown schematically in FIG. 3A, consisted of three differentially-pumped chambers, an electrospray ionization system (ESI) and a hexapole ion guide. The NEMS device was kept at the highest vacuum chamber of the three-chamber differential pumping setup, with a base pressure of 10$^{-5}$ Torr prior to cryo-pumping.

ESI experiments with gold nanoparticles were carried out by injecting solution into a needle (0.3 mm in radius) that was biased at 4 kV. This large voltage caused the emission of charged microdroplets, which subsequently underwent cycles of evaporation and Coulombic fission, until individual ionized particles emerged in the gas phase. The distance between the needle top and the vacuum system inlet was about 1 cm. The capillary-skimmer voltage difference was about 180V.

These ions were transported into the first chamber of the vacuum system by hydrodynamic flow and electrostatic focusing. Near the entrance of the vacuum system, hot N$_2$ gas flowed counter to the incoming material, which swept away neutral molecules and dried out the microdroplets, enhancing Coulombic fission. Once the particles entered into the vacuum system, they traveled through the capillary toward the first stage of the vacuum chamber. At the end of the tube, the incoming gas expanded into a low vacuum region where it was supersonically accelerated. The ions were then sampled by a skimmer structure to obtain a collimated molecular/ionic beam. The larger particles in the molecular beam were slowed down in the second chamber (at 10 mTorr) through collisions with background atoms. This decelerated beam was focused to the third chamber (main chamber) where the NEMS device was placed. The hexapolar ion guides were driven by alternating RF signals with 350-500 kHz frequencies and 300-360V amplitudes.

For the ESI experiments with IgM, several parameters were changed to facilitate the analysis of the protein complex. The ESI needle for IgM experiments had a tip diameter of 20 µm (Picotip Emitter, New Objective) and was placed about 1 cm away from the vacuum system inlet. The N$_2$ gas was not heated for IgM experiments. The capillary-skimmer voltage difference was decreased to 30V to avoid excessive acceleration of the ions. The pressure in the collisional focusing cell was elevated to 50 mTorr to facilitate the deceleration of the ions. The hexapolar ion guides were driven by alternating RF signals with 350-500 kHz frequencies and 300-360V amplitudes.

Example 4

MALDI NEMS-MS

NEMS-MS experiments employing MALDI delivery were carried out in a chamber (Kurt Lesker) within a table-top ultra-high vacuum capable apparatus equipped with a flow cryostat (Janis) (shown schematically at FIG. 3B). A NEMS resonator was mounted to a sample stage and placed near the center of the chamber. The sample stage was cooled to 80K by liquid Nitrogen from the cryostat. The MALDI sample plate was positioned inside the vacuum chamber at a distance of approximately 5 mm from the NEMS resonator on a computer controlled x,y-translation stage (Kurt Lesker).

A nitrogen laser (model NL 100 from Stanford Research Systems) was focused through a 400 mm lens (Thorlabs) to a ~50×100 µm$^2$ spot that illuminated the backside of the sample plate. The laser was operated at a wavelength of 337 nm, 170 µJ/pulse, 3.5 ns pulse width and a repetition rate of 1 Hz. The chamber was maintained at a base pressure of 10$^{-9}$ Torr.

The MALDI sample plate was moved relative to the laser spot using the x-y stage. The laser ionized the sample, and particles emitted in the MALDI plume then accreted upon the NEMS resonator. No ionization optics were used, and the NEMS resonator collected both positive and negative ions, as well as neutrals, from the MALDI plume.

Example 5

LIAD NEMS-MS

A LIAD sample, with pre-deposited surface proteins, was inserted onto the sample holder in a UHV chamber (Kurt Lesker). The substrate sample holder was connected to a motorized, UHV x and y manipulator (Kurt Lesker), which also featured z-axis manual movement to adjust the sample- NEMS distance. The LIAD sample was held opposite to, and facing, a NEMS device mounted at the end of a UHV flow cryostat (Janis). The NEMS chip mounting consisted of a custom fabricated printed circuit board (PCB) to which the chip was attached with copper tape. The on-chip device leads were wire bonded to PCB leads attached to soldered SMA heads. The cryostat was used for vacuum cooling of the device. A laser spot was previously aligned to the NEMS device using a transparent substrate without protein sample. During each experimental run, the distance between the LIAD substrate and the NEMS device was fixed at about 2 to 3 cm.

For each experiment, the laser was constantly pulsed at 1 Hz while the substrate was scanned in x and y directions. Each laser pulse produced a plume of protein material towards the device, causing individual proteins randomly land on the device. At the same time, the device remained in a phase-locked loop (PLL) to track the 2-mode resonance frequencies in real time. When a protein landed on the device, simultaneous frequency jumps were recorded in each mode. These jump pairs were used to calculate the mass and position of each particle that landed on the device. The 1 Hz pulse rate of the laser was set to ensure that multiple proteins would not land on the device during the PLL time constant (250 ms).

Example 6

NEMS-MS Data Acquisition

The NEMS resonators used in this work were controlled and monitored using multimode readout circuitry schematically depicted in FIG. 1. A piezoresistive down-conversion method was employed for the transduction of mechanical motion, where electrostatic actuation was achieved using proximal capacitive gates, and resonator motion was transduced using symmetric semiconducting piezoresistive strain gauges located near both ends of the device.
GNP ESI NEMS-MS For the ESI work with GNPs, the circuitry followed that in Bargatin et al., 90 *Applied Physics Letter* 093116 (2007), with additional components (power combiners and filters) to transduce two modes simultaneously. The device was calibrated by using the adsorption rate of water vapour on the device at decreased temperatures (30K). In the ESI system, water vapour is the dominant background gas, and its partial pressure was measured by a residual gas analyzer. This partial pressure information was then translated into accretion rate on the nanodevice. From the rate of mass accretion and the frequency change, the responsivity of the device was calibrated.

Gold electrodes patterned on the beam were used to actuate and measure the mechanical motion via thermoelastic actuation and piezoresistive detection, respectively. For each mode, one function generator (Rhode and Schwartz model SM03) was used to excite a drive electrode at half the resonance frequency and another function generator was used to bias a readout electrode at a frequency slightly detuned from the drive resonance. These two signals generated a mix-down signal of mechanical origin at the readout electrode when the drive frequency matched exactly half the mechanical resonance frequency. This low-frequency readout signal was amplified and fed into a lock-in amplifier (Signal Recovery model 5210) with a matching external reference generated from the two function generators.
MALDI NEMS-MS and IgM ESI NEMS-MS MALDI and IgM ESI experiments were performed without any device calibration. For MALDI-based experiments and ESI-based IgM experiments, the modes were actuated using Agilent (model N5181A) and Rhode and Schwartz (SM03) function generators. For each mode the drive and bias signals were split. On one path, the bias and drive signals were mixed and the output was used as a reference for the lock-in amplifier (Stanford Research Systems model SR830). On the other path, the drive signals for both modes were combined together with a DC source and the total signal $(V_1(\omega_{d1})+V_2(\Omega_{d2})+V_{DC})$ was sent to a gate electrode that capacitively actuated the device. Meanwhile, the bias signals for each mode were split in a 180° splitter and the same-polarity signals of both modes were combined and sent to the device. At the device, the bias 1 electrode was charged to $V_1^+(\omega_{b1})+V_2^+(\omega_{b2})$ and the bias 2 electrode was charged to $V_1^-(\omega_{b1})+V_2^-(\omega_{b2})$. A control loop was implemented by reading the lock-in amplifier signal on a computer that performed a corrector calculation and then sent a control signal to the function generators. Details of the corrector calculation are given in Kharrat, C. et al., *Sensors*, 2008 *IEEE* 1135-38. The lock-in amplifiers and the function generators were connected to the computer by a GPIB interface. In this manner, the computer controlled the instruments without being connected to the RF signals that were sent to the device.

LIAD NEMS-MS

Data acquisition for LIAD NEMS-MS mirrored the data acquisition for MALDI NEMS-MS, as described above.

Example 7

Analyte Mass and Position Determination

Data for a first and a second mode were acquired as described above. For the ESI-based IgM experiment, the Allan deviation characterizing the frequency fluctuations of the first NEMS mode was $\sigma_A^{(1)} \sim 8 \times 10^{-8}$, and of the second mode was $\sigma_A^{(2)} \sim 1 \times 10^{-7}$ at the chosen phase-locked loop (PLL) response time of $\tau_R \sim 500$ milliseconds unless noted otherwise.

For measurements of the 10 nm GNPs with the ESI system, obtained with a previous generation of smaller devices, these values were $\sigma_A^{(1)} \sim 3 \times 10^{-6}$ and $\sigma_A^{(2)} \sim 2 \times 10^{-6}$ at $\tau_R \sim 10$ seconds. (A longer response time was required with the earlier generation of instrumentation used.) These frequency fluctuations yielded a mass resolution of approximately 50 kDa and 100 kDa for these two sets of measurements, respectively. The measured noise correlation between the modes was ~0.3 (~0.7 for the first generation system and devices). FIG. 4A shows a snapshot of two-mode PLL data obtained during electrospray ionization of 10 nm GNPs. FIG. 4B shows a snapshot of two-mode PLL data from human IgM obtained with ESI delivery. Time-correlated, quasi-instantaneous frequency jumps of different heights in the two modes allowed resolution of discrete adsorption events from individual molecules or nanoparticles accreted onto the NEMS resonator. These experimentally obtained frequency jumps were used to determine the mass and position of each molecule/nanoparticle by mapping the $$\left(\frac{\delta f_1}{f_1}, \frac{\delta f_2}{f_2}\right)$$

pairs onto the $$\frac{\delta m}{M},$$

a plane as described above.

Both ESI and MALDI NEMS-MS experiments were performed with 10 nm GNPs. FIG. 6B shows the mass spectra of 10 nm GNPs delivered to the resonator via ESI (gray, open circles) and MALDI (black, open circles). The data for the MALDI curve was analyzed with the same experimental mass resolution that was achieved with the ESI setup for 10 nm gold nanoparticles. Also shown are the best-fit curves for each data set (solid lines). For the ESI data, the best fit (gray, solid line) yielded a diameter of 9.8 nm and standard deviation of 2.5 nm, while the data using MALDI (black, solid line) yielded a diameter of 10.7 nm and a standard deviation of 2.8 nm. These values are within the experimental deviation of the vendor specifications for the GNPs.

MALDI-based measurements were performed with 5 nm GNPs. In these experiments two types of MALDI plates were prepared; each containing 5 nm GNPs, but differing in whether glycerol was added as a separating agent. FIG. 6C shows two distinct mass spectra for the two 5 nm GNP samples, where the patterned curve represents the sample with glycerol, and the solid curve represents the sample without glycerol. A clear reduction in GNP clustering is observed with the use of glycerol. FIG. 6A shows the accumulated mass spectra, as acquired particle-by-particle, for the 5 nm GNPs with glycerol. The mass was calculated for each analyte landing event in real-time.

Single-molecule NEMS-MS spectra were obtained for human IgM using ESI delivery. Experiments were performed without any calibration other than measuring the dimensions of the resonator. In serum, IgM is typically found in macromolecular complexes that are assembled by the immune system. The presently-known biologically-active isoforms in serum can be, for example, tetrameric (M4), pentameric (M5), hexameric (M6), or dipentameric assemblies of identical ~190 kDa subunits (M10). For the prevalent pentamer isoform, an additional small protein (the J chain) links the assemblage and contributes ~15 kDa to the total ~960 kDa mass of the complex.

Figure 6D:
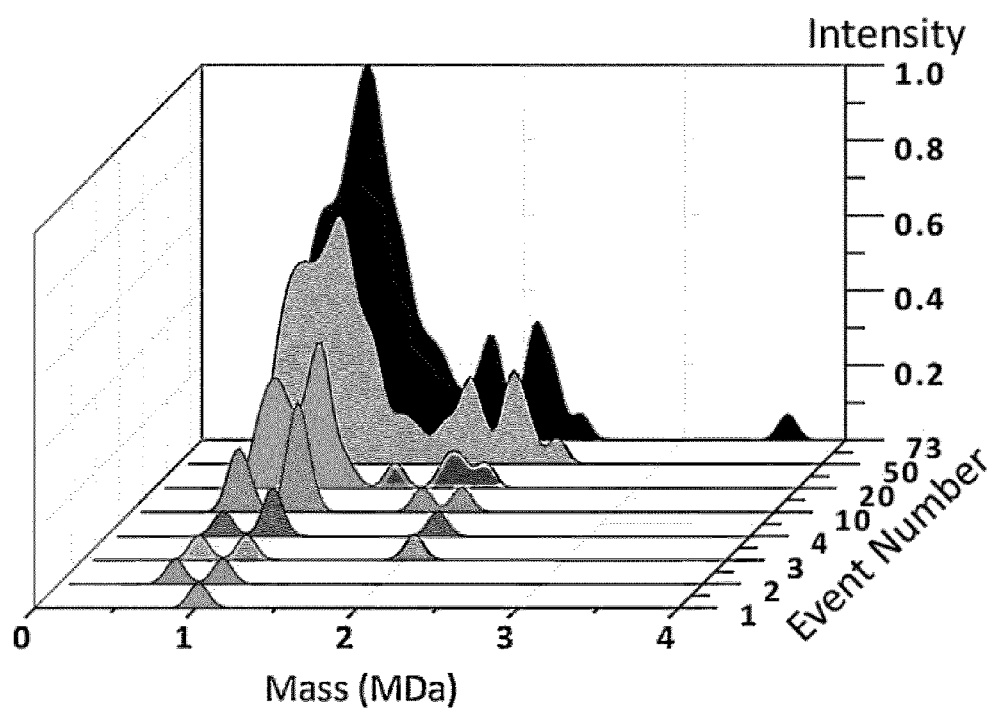
FIG. 6D shows a mass spectrum of molecule-by-molecule landing of human IgM on a NEMS resonator, where analytes accumulating at different molecular weights correspond to different isoforms of the molecule, and where the total cumulative spectrum (black, at back) is the additive result of 74 individually measured molecules.
Figure 6E:
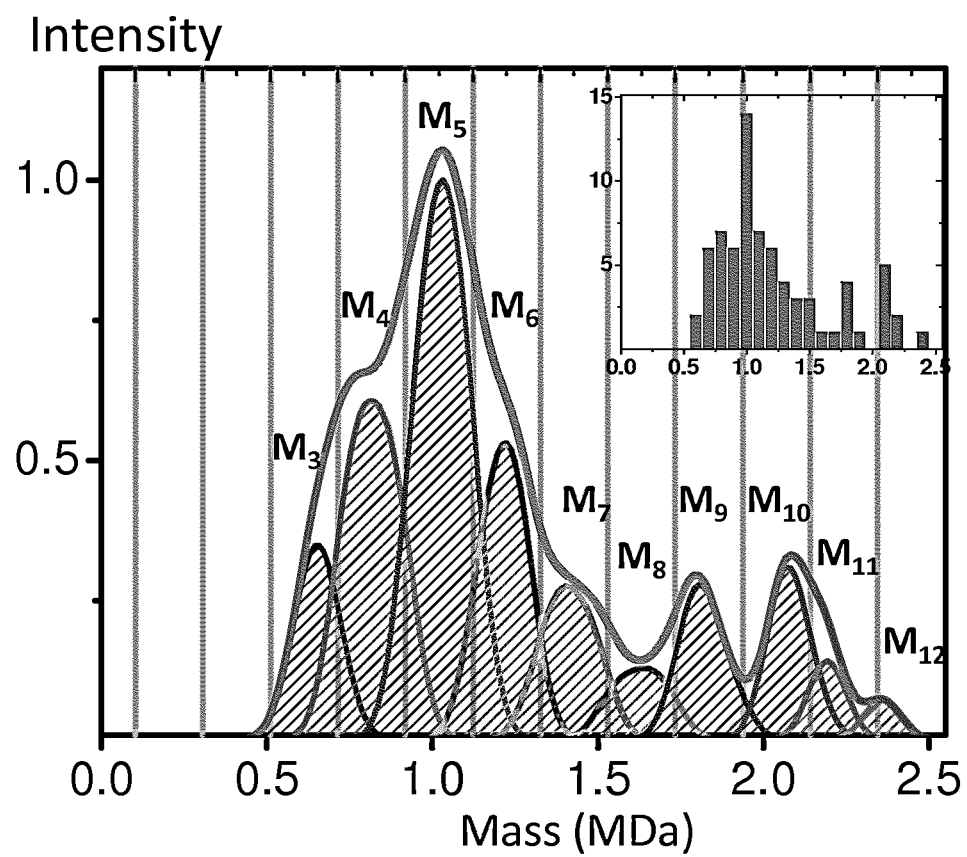
FIG. 6E shows a composite spectrum of an IgM sample, where the spectrum is decomposed into different polymerization levels of IgM, and the inset shows a histogram of the event masses binned according to mass resolution.

Mass spectra obtained for human IgM is shown in FIG. 6D-E. In an overall mass spectrum, a composite curve was accumulated from 74 single particle spectra. The individual pentameric IgM complex (the highest intensity peak) is clearly visible at 1.03±0.05 MDa, as is a dimerized pentameric complex ("dipentamer") at 2.09±0.05 MDa—a ratio very close to two, as expected (FIG. 6E). These measured values are close to the anticipated values 0.96 MDa and 1.92 MDa. Each single particle/molecule event was resolved with its own uncertainty level.

The well-resolved, individual single-unit peaks in FIG. 6E is experimental data—and the overarching curve is the numerical integral of the data. The spectrum eliminates typical ambiguities in identifying and explaining the origin of spectral features, such as the apparent shoulder at 0.82 MDa in the composite intensity curve. The present data unambiguously indicate that the shoulder at 0.82 MDa arises from the presence of precisely twelve accreted macromolecular complexes, each tetramers of IgM, that individually landed on the NEMS mass resonator and were separately measured as part of the ensemble of 74 molecules collected during this experiment.

Due to mass measurement error, there is a small probability for some events to be misidentified when the noise level during that particular event happens to exceed the 2σ noise threshold separating two distinct species. We determined the number of potentially misidentified particles by performing a statistical analysis on the data ensemble. This analysis suggested that less than 7% of the events, that is, only ~5 of the 74 collected molecules, might be misidentified.

Figure 6F:
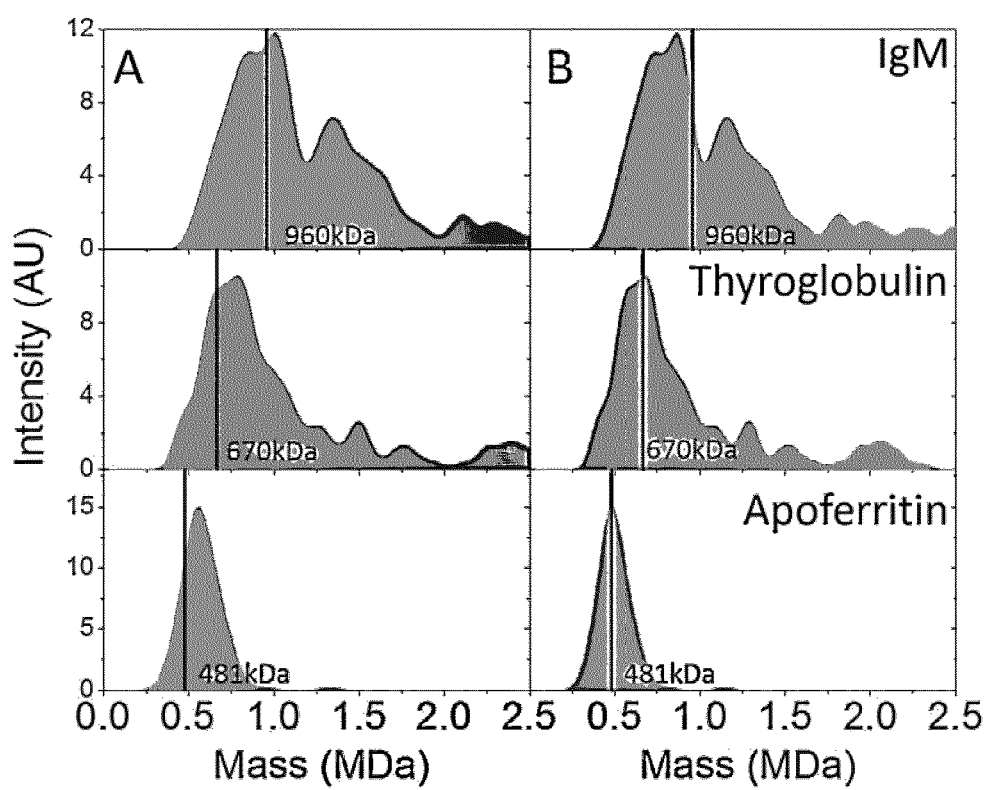
FIG. 6F shows a composite spectrum of IgM, thyroglobulin, and apoferritin, where the analytes were delivered to the resonator with a LIAD delivery system, and where the spectra in (a) are mass calibrated according to the device fabrication mask, and in (b) apoferritin is used as a calibration standard.

LIAD-based measurements were performed with IgM, thyroglobulin, and apoferritin. In one experiment, an apoferritin spectrum was used as a calibration standard. Mass spectra showing the cumulative results of many individual landing events (314 landing events for IgM, 144 landing events for thyroglobulin, and 119 landing events for apoferritin) is shown in FIG. 6F. FIG. 6F shows mass spectra with with (b) and without (a) calibration with apoferritin. The vertical black lines represent the expected mass of the nominally dominant isoforms. Without calibration, all three spectra are close to the expected results. For the IgM and thyroglobulin spectra, some intensity is seen at slightly higher mass values, which may be due to larger isoforms, clumped particles, or multiple particles landing on the device simultaneously. The dominant IgM peak at 1.00±0.05 MDa is within the uncertainty of the expected mass (0.96 MDa) of the dominant IgM isoform (the pentamer). Both thyroglobulin and apoferritin display a dominant peak close to, but outside the uncertainty range of the expected mass. In the case of thyroglobulin, there are evidently two peaks with similar intensity values that dominate the spectrum. The centroid of the slightly smaller peak, 0.67±0.05 MDa, exactly matches that of the theoretically dominant isoform (the tetramer). The more experimentally dominant peak, however, at a mass of 0.79±0.05 MDa, is within uncertainty of the next highest isoform, the pentamer with an expected mass of 0.835 MDA. For apoferritin, the observed peak mass of 0.56±0.05 MDa is outside uncertainty of the expected mass value of 0.48 MDa. When apoferritin is used as a calibration standard, as shown in FIG. 6F(b), the thyroglobulin spectrum is well matched between the dominant peak and the expected value.

Figure 6G:
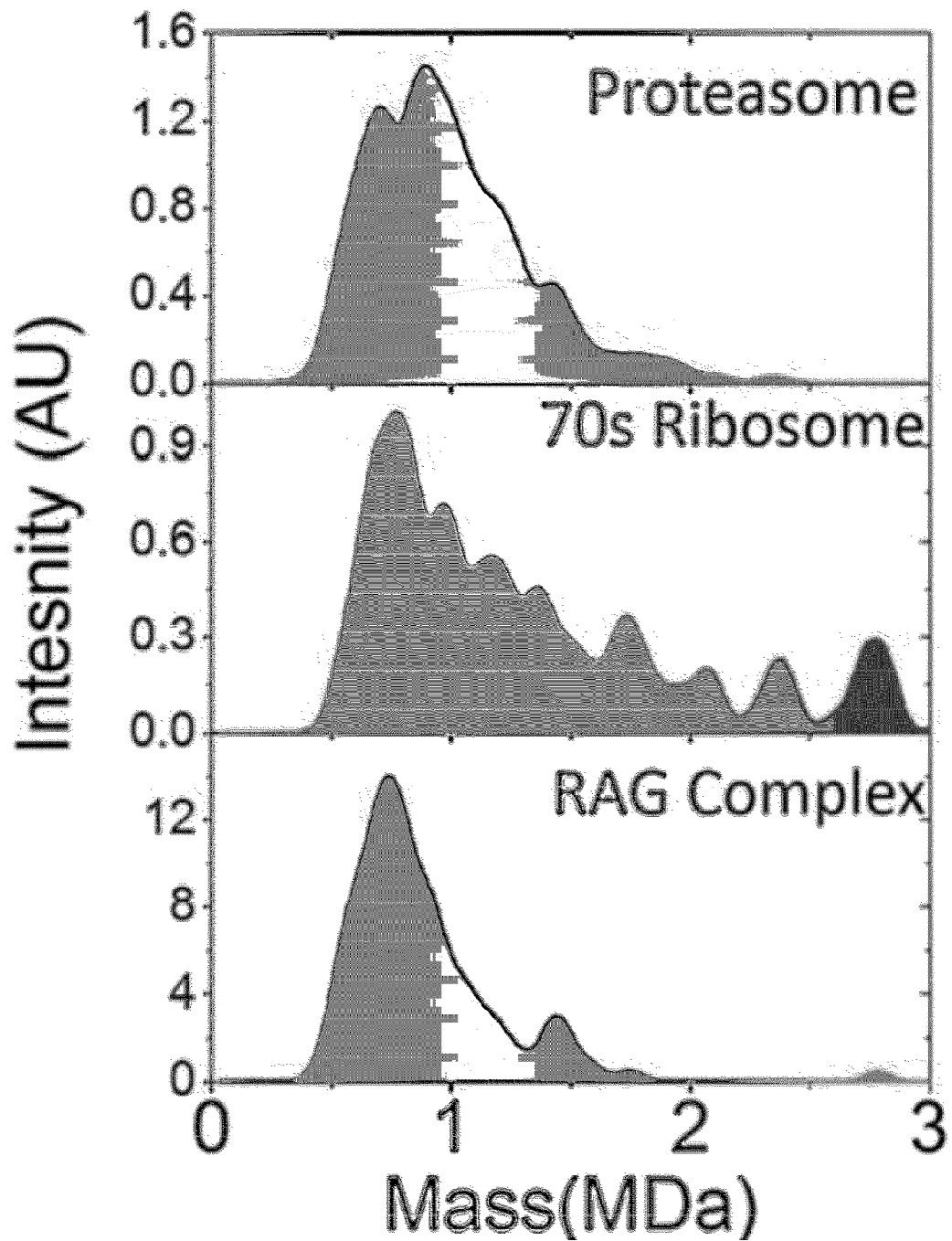
FIG. 6G shows a composite spectrum of proteasome, 70s ribosome, and RAG Complex, where the analytes were delivered to the resonator with a LIAD delivery system.

LIAD-based measurements were also performed with proteasome, 70s ribosome, and RAG complex, as shown in FIG. 6G. These data demonstrate the ability of the LIAD NEMS system to measure large protein complexes. In the cases of the proteasome and the 70s ribosome, the intact complexes at 2.5 MDa and 2.3 MDa, respectively, are fragmented into subcomponents. Meanwhile, for the RAG complex, which has a mass of 0.36 MDa, the dimer and tetramer of the intact complex are clearly distinguishable as separate peaks.

What is claimed is:

1. A method comprising:
    measuring a landing position and mass of an analyte adsorbed to a nanomechanical resonator by resolving adsorbate-induced frequency shifts in at least two modes of a resonator resonance frequency, wherein during the resolving of the frequency shifts in the at least two modes analysis is so that the transformation (G) from the fractional-frequency shift pair to the analyte mass-position pair is one-to-one.

2. The method of claim 1, wherein the measuring comprises transducing the resonator into motion at at least a first frequency mode and a second frequency mode and detecting the frequency shifts in the at least the first frequency mode and the second frequency mode upon adsorption of the analyte.

3. The method of claim 2, wherein the at least the first frequency mode and the second frequency mode are measured simultaneously.

4. The method of claim 3, wherein resonator transduction is controlled and monitored using multimode readout circuitry.

5. The method of claim 4, wherein for each mode, a first function generator induces a first signal by exciting a drive electrode at half the resonance frequency and a second function generator induces a second signal by biasing a readout electrode at a frequency slightly detuned from the frequency of the first signal, and wherein the first and second signals generate a mix-down signal of mechanical origin at the readout electrode when the drive frequency matches exactly half of the resonance frequency.

6. The method of claim 5, wherein a low-frequency readout signal is amplified and fed into a lock-in amplifier with a matching external reference generated from the two function generators.

7. The method of claim 4, wherein for the at least the first frequency mode and the second frequency mode, a drive signal and a bias signal are split onto a first path and a second path, and wherein:
  on the first path, the bias signal and the drive signal are mixed and an output signal is used as a reference for a lock-in amplifier; and
  on the second path, the drive signals for the at least the first frequency mode and the second frequency mode are combined together with a DC source and the total signal $(V_1(\omega_{d1})+V_2(\omega_{d2})+V_{DC})$ is sent to a gate electrode that capacitively actuates the resonator; and
  wherein the bias signals for the at least the first frequency mode and the second frequency mode are split in a 180° splitter and signals with the same polarity of both modes are combined into a bias 1 signal and a bias 2 signal and sent to the resonator; and
  wherein at the resonator, a bias 1 electrode is charged to $V_1^+(\omega_{b1})+V_2^+(\omega_{b2})$ and a bias 2 electrode is charged to $V_1^-(\omega_{b1})+V_2^-(\omega_{b2})$.

8. The method of claim 7, wherein a control loop is implemented by reading a signal from the lock-in amplifier on a computer that performs a corrector calculation and sends the signals to the function generators, wherein the lock-in amplifiers and the function generators are connected to the computer by a GPIB interface, and wherein the computer controls the instruments without being connected to the RF signals that are sent to the device.

9. The method of claim 1, wherein the induced frequency shift in the at least the first frequency mode and the second frequency mode is modeled as a random variable with a mean value commensurate with the measured shift and with a dispersion identical with that of the frequency noise.

10. The method of claim 9, wherein frequency noise statistics for the first frequency mode and the second frequency mode are combined into a joint probability density function (JPDF) represented by the formula $$JPDF_{\delta f_1, \delta f_2}(\delta f_1, \delta f_2) = \frac{1}{2\pi\sigma_1\sigma_2\sqrt{(1-\rho^2)}} \exp\left(-\frac{z}{2(1-\rho^2)}\right),$$

where $$z \equiv \frac{(\delta f_1 - \mu_1)^2}{\sigma_1^2} - \frac{2\rho(\delta f_1 - \mu_1)(\delta f_2 - \mu_2)}{\sigma_1\sigma_2} + \frac{(\delta f_2 - \mu_2)^2}{\sigma_2^2},$$

$\delta f_1$ and $\delta f_2$ are the normalized frequency shifts in the first and second modes, respectively, $\mu_1$ and $\mu_2$ are mean values for frequency fluctuations in the first and second modes, respectively, $\sigma_1$ and $\sigma_2$ are standard deviations of the first and second modes, respectively, and $\rho$ is the correlation coefficient between the frequency noise in the two modes.

11. The method of claim 10, wherein a $|\delta f_1/f_1|, |\delta f_2/f_2|$ plane is mapped onto a $(\delta m/M, a)$ plane and a JPDF for mass and position, $JPDF_{\delta m, a}(\delta m, a)$ is calculated.

12. The method of claim 11, wherein the JPDF is used to determine the probability distribution of mass using the following formula:

$$PDF_{\delta m}(\delta m) = \int_{a=0}^{a=0.5} JPDF_{\delta m, a}(\delta m, a) da.$$

13. The method of claim 11, wherein the JPDF is used to determine the probability distribution of position using the following formula:

$$PDF_a(a) = \int_{\delta m=0}^{\delta m=\infty} JPDF_{\delta m, a}(\delta m, a) d(\delta m).$$

14. The method of claim 11, wherein a frequency jump due to an analyte landing is represented by a displacement of a noise JPDF by a vector formed by the two frequency shifts.

15. The method of claim 11, wherein $JPDF_{\delta m, a}(\delta m, a) = |J| \times JPDF_{\delta f_1, \delta f_2}(h_1(\delta m, a), h_2(\delta m, a))$ wherein, $h_1(\delta m, a) = -\delta m \, \phi_1(a)^2/\alpha_1$ and $h_2(\delta m, a) = -\delta m \, \phi_2(a)^2/\alpha_2$, where $\phi_n(a)$ is the $n^{th}$ resonance mode shape at a landing position, a, with a normalization condition $\max(\phi_n(a))=1$, $\alpha_n$ is a numerical factor defined as $$\alpha_n = 2\int_{a=0}^{a=1} \phi_n(a)^2 da,$$

wherein $\alpha_n$ characterizes an effective mass, $M_{eff}^{(n)} = (\alpha_n/2)M_{total}$, for each mode; and $|J|$ is a positive determinant of the matrix:

$$|J| = \text{abs}\left(\frac{\partial h_1}{\partial(\delta m)}\frac{\partial h_2}{\partial a} - \frac{\partial h_2}{\partial(\delta m)}\frac{\partial h_1}{\partial a}\right).$$

16. The method of claim 11, wherein mass and position are calculated from the JPDF according to the following formula:

$$JPDF_{\delta m, a}(\delta m, a) = |J| \times \frac{1}{2\pi\sigma_1\sigma_2\sqrt{(1-\rho^2)}} \exp\left(-\frac{\Gamma}{2(1-\rho^2)}\right)$$

wherein $$|J| = \frac{2\delta m}{\alpha_1\alpha_2}[\phi_1(a)\phi_2(a)]\left|\frac{\partial\phi_1}{\partial\eta}\right|_{\eta=a}\phi_2(a) - \left.\frac{\partial\phi_2}{\partial\eta}\right|_{\eta=a}\phi_1(a)\right|,$$

and $$\Gamma = \frac{\left(\frac{\delta m \phi_1(a)^2}{\alpha_1} + \mu_1\right)^2}{\sigma_1^2} - \frac{2\rho\left(\frac{\delta m \phi_1(a)^2}{\alpha_1} + \mu_1\right)\left(\frac{\delta m \phi_2(a)^2}{\alpha_2} + \mu_2\right)}{\sigma_1\sigma_2} + \frac{\left(\frac{\delta m \phi_2(a)^2}{\alpha_2} + \mu_2\right)^2}{\sigma_2^2}.$$

17. The method of claim 1, wherein the method is performed at temperature of about 70K to about 140K.

18. The method of claim 1, wherein the frequency shift is a downshift.

19. The method of claim 1, further comprising delivering the analyte to the resonator prior to measuring the landing position and mass of the analyte.

20. The method of claim 19, wherein the delivering is performed by an electrospray ionization delivery system.

21. The method of claim 19, wherein the delivering is performed by a MALDI delivery system.

22. The method of claim 21, wherein the MALDI delivery system delivers one or more of positively charged, negatively charged, or neutral particles to the resonator.

23. The method of claim 1, wherein the mass of the analyte is about a few Daltons or more.

24. The method of claim 1, wherein the mass of the analyte is about 500 kDa or more.

25. The method of claim 1, wherein the mass of the analyte is in the MDa range.

26. The method of claim 1, wherein the adsorption is physisorption.

27. The method of claim 1, wherein the analyte is one or more of an individual molecule, a molecular complex, an isoform, or a nanoparticle.

28. The method of claim 1, wherein the at least two modes are phase locked.

29. The method of claim 1, wherein the landing position is measured only when the analyte adsorbs in the center 50% of the resonator.

30. The method of claim 1, wherein the resonator is a doubly-clamped beam, and wherein analysis is restricted to one half of the beam's length.

31. The method of claim 1, wherein the resonator is a cantilever, and wherein the measuring comprises transducing the cantilever into motion at at least a first frequency mode, a second frequency mode, and a third frequency mode and detecting the frequency shifts in the at least first, second, and third modes upon adsorption of the analyte.

32. The method of claim 1, wherein the measuring is performed in real-time.

33. The method of claim 1, wherein the analyte is in a complex mixture.

34. The method of claim 33, wherein the complex mixture comprises a plurality of analytes.

35. The method of claim 1, wherein the delivering is performed by a LIAD delivery system.

36. The method of claim 35, wherein the LIAD system delivers one or more neutral molecules to the resonator.

37. An apparatus for measuring a mass of a sample comprising: (i) a NEMS resonator arranged to receive the sample delivered to the resonator at a landing position, and (ii) a LIAD delivery system.

38. The apparatus of claim 37, wherein changes in the frequency of vibration of the resonator indicate a magnitude of mass added to the resonator.

39. The apparatus of claim 37, wherein the sample comprises one or more analytes.

40. A method of measuring the mass of at least one analyte comprising: delivering the analyte to a resonator with a LIAD delivery system, receiving the analyte onto a NEMS resonator at a landing position, and detecting a vibration frequency of the resonator to measure an absorbed mass of the analyte.

* * * * *